(12) United States Patent
Raman et al.

(10) Patent No.: US 11,125,885 B2
(45) Date of Patent: Sep. 21, 2021

(54) MONITORING USER BIOMETRIC PARAMETERS WITH NANOTECHNOLOGY IN PERSONAL LOCATOR BEACON

(71) Applicant: Hand Held Products, Inc., Fort Mill, SC (US)

(72) Inventors: Kannan Raman, Madurai (IN); Sai Bhanu Prakash Thupalli, Telangana (IN)

(73) Assignee: HAND HELD PRODUCTS, INC., Fort Mill, SC (US)

( * ) Notice: Subject to any disclaimer, the term of this patent is extended or adjusted under 35 U.S.C. 154(b) by 203 days.

(21) Appl. No.: 15/279,481

(22) Filed: Sep. 29, 2016

(65) Prior Publication Data

US 2017/0265758 A1    Sep. 21, 2017

(30) Foreign Application Priority Data

Mar. 15, 2016 (IN) .............................. 201611009035

(51) Int. Cl.
*G01S 19/17* (2010.01)
*A61B 5/11* (2006.01)
(Continued)

(52) U.S. Cl.
CPC .......... *G01S 19/17* (2013.01); *A61B 5/02055* (2013.01); *A61B 5/1112* (2013.01);
(Continued)

(58) Field of Classification Search
CPC ........ G01S 19/17; G01S 19/18; G01S 5/0231; A61B 5/1112
See application file for complete search history.

(56) References Cited

U.S. PATENT DOCUMENTS

| 5,854,605 A | * | 12/1998 | Gildea | G01S 19/235 |
| | | | | 342/357.62 |
| 6,262,655 B1 | * | 7/2001 | Yoshioka | G08B 25/016 |
| | | | | 340/425.5 |

(Continued)

FOREIGN PATENT DOCUMENTS

| JP | 04113984 A | * | 4/1992 |
| JP | 2004038634 A | * | 2/2004 |

(Continued)

OTHER PUBLICATIONS

U.S. Appl. No. 14/715,916 for Evaluating Image Values filed May 19, 2015 (Ackley); 60 pages.

(Continued)

*Primary Examiner* — Cassi J Galt
(74) *Attorney, Agent, or Firm* — Alston & Bird LLP

(57) ABSTRACT

A personal locator beacon system has a personal locator beacon and a biometrics monitor. The personal locator beacon includes a first microprocessor, a first global positioning subsystem coupled to the first microprocessor, a first low energy transceiver coupled to the first microprocessor, and a first low energy antennae coupled to the first low energy transceiver. The biometrics monitor includes a second microprocessor, a second low energy transceiver coupled to the second microprocessor, a second low energy antennae coupled to the second low energy transceiver, and one or more nanosensors.

24 Claims, 5 Drawing Sheets

(51) Int. Cl.
  *G01S 5/02* (2010.01)
  *A61B 5/02* (2006.01)
  *G01S 19/32* (2010.01)
  *A61B 5/0205* (2006.01)
  *A61B 5/00* (2006.01)
  *A61B 5/01* (2006.01)

(52) U.S. Cl.
  CPC .......... *A61B 5/6824* (2013.01); *G01S 5/0231* (2013.01); *G01S 19/32* (2013.01); *A61B 5/01* (2013.01)

(56) References Cited

U.S. PATENT DOCUMENTS

| | | |
|---|---|---|
| 6,492,906 B1 | 12/2002 | Richards et al. |
| 6,832,725 B2 | 12/2004 | Gardiner et al. |
| 7,128,266 B2 | 10/2006 | Zhu et al. |
| 7,159,783 B2 | 1/2007 | Walczyk et al. |
| 7,413,127 B2 | 8/2008 | Ehrhart et al. |
| 7,726,575 B2 | 6/2010 | Wang et al. |
| 8,294,969 B2 | 10/2012 | Plesko |
| 8,317,105 B2 | 11/2012 | Kotlarsky et al. |
| 8,322,622 B2 | 12/2012 | Liu |
| 8,366,005 B2 | 2/2013 | Kotlarsky et al. |
| 8,371,507 B2 | 2/2013 | Haggerty et al. |
| 8,376,233 B2 | 2/2013 | Van Horn et al. |
| 8,381,979 B2 | 2/2013 | Franz |
| 8,390,909 B2 | 3/2013 | Plesko |
| 8,408,464 B2 | 4/2013 | Zhu et al. |
| 8,408,468 B2 | 4/2013 | Horn et al. |
| 8,408,469 B2 | 4/2013 | Good |
| 8,424,768 B2 | 4/2013 | Rueblinger et al. |
| 8,448,863 B2 | 5/2013 | Xian et al. |
| 8,457,013 B2 | 6/2013 | Essinger et al. |
| 8,459,557 B2 | 6/2013 | Havens et al. |
| 8,469,272 B2 | 6/2013 | Kearney |
| 8,474,712 B2 | 7/2013 | Kearney et al. |
| 8,479,992 B2 | 7/2013 | Kotlarsky et al. |
| 8,490,877 B2 | 7/2013 | Kearney |
| 8,517,271 B2 | 8/2013 | Kotlarsky et al. |
| 8,523,076 B2 | 9/2013 | Good |
| 8,528,818 B2 | 9/2013 | Ehrhart et al. |
| 8,544,737 B2 | 10/2013 | Gomez et al. |
| 8,548,420 B2 | 10/2013 | Grunow et al. |
| 8,550,335 B2 | 10/2013 | Samek et al. |
| 8,550,354 B2 | 10/2013 | Gannon et al. |
| 8,550,357 B2 | 10/2013 | Kearney |
| 8,556,174 B2 | 10/2013 | Kosecki et al. |
| 8,556,176 B2 | 10/2013 | Van Horn et al. |
| 8,556,177 B2 | 10/2013 | Hussey et al. |
| 8,559,767 B2 | 10/2013 | Barber et al. |
| 8,561,895 B2 | 10/2013 | Gomez et al. |
| 8,561,903 B2 | 10/2013 | Sauerwein |
| 8,561,905 B2 | 10/2013 | Edmonds et al. |
| 8,565,107 B2 | 10/2013 | Pease et al. |
| 8,571,307 B2 | 10/2013 | Li et al. |
| 8,579,200 B2 | 11/2013 | Samek et al. |
| 8,583,924 B2 | 11/2013 | Caballero et al. |
| 8,584,945 B2 | 11/2013 | Wang et al. |
| 8,587,595 B2 | 11/2013 | Wang |
| 8,587,697 B2 | 11/2013 | Hussey et al. |
| 8,588,869 B2 | 11/2013 | Sauerwein et al. |
| 8,590,789 B2 | 11/2013 | Nahill et al. |
| 8,596,539 B2 | 12/2013 | Havens et al. |
| 8,596,542 B2 | 12/2013 | Havens et al. |
| 8,596,543 B2 | 12/2013 | Havens et al. |
| 8,599,271 B2 | 12/2013 | Havens et al. |
| 8,599,957 B2 | 12/2013 | Peake et al. |
| 8,600,158 B2 | 12/2013 | Li et al. |
| 8,600,167 B2 | 12/2013 | Showering |
| 8,602,309 B2 | 12/2013 | Longacre et al. |
| 8,608,053 B2 | 12/2013 | Meier et al. |
| 8,608,071 B2 | 12/2013 | Liu et al. |
| 8,611,309 B2 | 12/2013 | Wang et al. |
| 8,615,487 B2 | 12/2013 | Gomez et al. |
| 8,621,123 B2 | 12/2013 | Caballero |
| 8,622,303 B2 | 1/2014 | Meier et al. |
| 8,628,013 B2 | 1/2014 | Ding |
| 8,628,015 B2 | 1/2014 | Wang et al. |
| 8,628,016 B2 | 1/2014 | Winegar |
| 8,629,926 B2 | 1/2014 | Wang |
| 8,630,491 B2 | 1/2014 | Longacre et al. |
| 8,635,309 B2 | 1/2014 | Berthiaume et al. |
| 8,636,200 B2 | 1/2014 | Kearney |
| 8,636,212 B2 | 1/2014 | Nahill et al. |
| 8,636,215 B2 | 1/2014 | Ding et al. |
| 8,636,224 B2 | 1/2014 | Wang |
| 8,638,806 B2 | 1/2014 | Wang et al. |
| 8,640,958 B2 | 2/2014 | Lu et al. |
| 8,640,960 B2 | 2/2014 | Wang et al. |
| 8,643,717 B2 | 2/2014 | Li et al. |
| 8,646,692 B2 | 2/2014 | Meier et al. |
| 8,646,694 B2 | 2/2014 | Wang et al. |
| 8,657,200 B2 | 2/2014 | Ren et al. |
| 8,659,397 B2 | 2/2014 | Vargo et al. |
| 8,668,149 B2 | 3/2014 | Good |
| 8,678,285 B2 | 3/2014 | Kearney |
| 8,678,286 B2 | 3/2014 | Smith et al. |
| 8,682,077 B1 | 3/2014 | Longacre |
| D702,237 S | 4/2014 | Oberpriller et al. |
| 8,687,282 B2 | 4/2014 | Feng et al. |
| 8,692,927 B2 | 4/2014 | Pease et al. |
| 8,695,880 B2 | 4/2014 | Bremer et al. |
| 8,698,949 B2 | 4/2014 | Grunow et al. |
| 8,702,000 B2 | 4/2014 | Barber et al. |
| 8,717,494 B2 | 5/2014 | Gannon |
| 8,720,783 B2 | 5/2014 | Biss et al. |
| 8,723,804 B2 | 5/2014 | Fletcher et al. |
| 8,723,904 B2 | 5/2014 | Marty et al. |
| 8,727,223 B2 | 5/2014 | Wang |
| 8,740,082 B2 | 6/2014 | Wilz |
| 8,740,085 B2 | 6/2014 | Furlong et al. |
| 8,746,563 B2 | 6/2014 | Hennick et al. |
| 8,750,445 B2 | 6/2014 | Peake et al. |
| 8,752,766 B2 | 6/2014 | Xian et al. |
| 8,756,059 B2 | 6/2014 | Braho et al. |
| 8,757,495 B2 | 6/2014 | Qu et al. |
| 8,760,563 B2 | 6/2014 | Koziol et al. |
| 8,763,909 B2 | 7/2014 | Reed et al. |
| 8,777,108 B2 | 7/2014 | Coyle |
| 8,777,109 B2 | 7/2014 | Oberpriller et al. |
| 8,779,898 B2 | 7/2014 | Havens et al. |
| 8,781,520 B2 | 7/2014 | Payne et al. |
| 8,783,573 B2 | 7/2014 | Havens et al. |
| 8,789,757 B2 | 7/2014 | Barten |
| 8,789,758 B2 | 7/2014 | Hawley et al. |
| 8,789,759 B2 | 7/2014 | Xian et al. |
| 8,794,520 B2 | 8/2014 | Wang et al. |
| 8,794,522 B2 | 8/2014 | Ehrhart |
| 8,794,525 B2 | 8/2014 | Amundsen et al. |
| 8,794,526 B2 | 8/2014 | Wang et al. |
| 8,798,367 B2 | 8/2014 | Ellis |
| 8,807,431 B2 | 8/2014 | Wang et al. |
| 8,807,432 B2 | 8/2014 | Van Horn et al. |
| 8,820,630 B2 | 9/2014 | Qu et al. |
| 8,822,848 B2 | 9/2014 | Meagher |
| 8,824,692 B2 | 9/2014 | Sheerin et al. |
| 8,824,696 B2 | 9/2014 | Braho |
| 8,842,849 B2 | 9/2014 | Wahl et al. |
| 8,844,822 B2 | 9/2014 | Kotlarsky et al. |
| 8,844,823 B2 | 9/2014 | Fritz et al. |
| 8,849,019 B2 | 9/2014 | Li et al. |
| D716,285 S | 10/2014 | Chaney et al. |
| 8,851,383 B2 | 10/2014 | Yeakley et al. |
| 8,854,633 B2 | 10/2014 | Laffargue |
| 8,866,963 B2 | 10/2014 | Grunow et al. |
| 8,868,421 B2 | 10/2014 | Braho et al. |
| 8,868,519 B2 | 10/2014 | Maloy et al. |
| 8,868,802 B2 | 10/2014 | Barten |
| 8,868,803 B2 | 10/2014 | Caballero |
| 8,870,074 B1 | 10/2014 | Gannon |
| 8,879,639 B2 | 11/2014 | Sauerwein |
| 8,880,426 B2 | 11/2014 | Smith |
| 8,881,983 B2 | 11/2014 | Havens et al. |

(56) References Cited

U.S. PATENT DOCUMENTS

| | | |
|---|---|---|
| 8,881,987 B2 | 11/2014 | Wang |
| 8,903,172 B2 | 12/2014 | Smith |
| 8,908,995 B2 | 12/2014 | Benos et al. |
| 8,910,870 B2 | 12/2014 | Li et al. |
| 8,910,875 B2 | 12/2014 | Ren et al. |
| 8,914,290 B2 | 12/2014 | Hendrickson et al. |
| 8,914,788 B2 | 12/2014 | Pettinelli et al. |
| 8,915,439 B2 | 12/2014 | Feng et al. |
| 8,915,444 B2 | 12/2014 | Havens et al. |
| 8,916,789 B2 | 12/2014 | Woodburn |
| 8,918,250 B2 | 12/2014 | Hollifield |
| 8,918,564 B2 | 12/2014 | Caballero |
| 8,925,818 B2 | 1/2015 | Kosecki et al. |
| 8,939,374 B2 | 1/2015 | Jovanovski et al. |
| 8,942,480 B2 | 1/2015 | Ellis |
| 8,944,313 B2 | 2/2015 | Williams et al. |
| 8,944,327 B2 | 2/2015 | Meier et al. |
| 8,944,332 B2 | 2/2015 | Harding et al. |
| 8,950,678 B2 | 2/2015 | Germaine et al. |
| D723,560 S | 3/2015 | Zhou et al. |
| 8,967,468 B2 | 3/2015 | Gomez et al. |
| 8,971,346 B2 | 3/2015 | Sevier |
| 8,976,030 B2 | 3/2015 | Cunningham et al. |
| 8,976,368 B2 | 3/2015 | Akel et al. |
| 8,978,981 B2 | 3/2015 | Guan |
| 8,978,983 B2 | 3/2015 | Bremer et al. |
| 8,978,984 B2 | 3/2015 | Hennick et al. |
| 8,985,456 B2 | 3/2015 | Zhu et al. |
| 8,985,457 B2 | 3/2015 | Soule et al. |
| 8,985,459 B2 | 3/2015 | Kearney et al. |
| 8,985,461 B2 | 3/2015 | Gelay et al. |
| 8,988,578 B2 | 3/2015 | Showering |
| 8,988,590 B2 | 3/2015 | Gillet et al. |
| 8,991,704 B2 | 3/2015 | Hopper et al. |
| 8,996,194 B2 | 3/2015 | Davis et al. |
| 8,996,384 B2 | 3/2015 | Funyak et al. |
| 8,998,091 B2 | 4/2015 | Edmonds et al. |
| 9,002,641 B2 | 4/2015 | Showering |
| 9,007,368 B2 | 4/2015 | Laffargue et al. |
| 9,010,641 B2 | 4/2015 | Qu et al. |
| 9,015,513 B2 | 4/2015 | Murawski et al. |
| 9,016,576 B2 | 4/2015 | Brady et al. |
| D730,357 S | 5/2015 | Fitch et al. |
| 9,022,288 B2 | 5/2015 | Nahill et al. |
| 9,030,964 B2 | 5/2015 | Essinger et al. |
| 9,033,240 B2 | 5/2015 | Smith et al. |
| 9,033,242 B2 | 5/2015 | Gillet et al. |
| 9,036,054 B2 | 5/2015 | Koziol et al. |
| 9,037,344 B2 | 5/2015 | Chamberlin |
| 9,038,911 B2 | 5/2015 | Xian et al. |
| 9,038,915 B2 | 5/2015 | Smith |
| D730,901 S | 6/2015 | Oberpriller et al. |
| D730,902 S | 6/2015 | Fitch et al. |
| D733,112 S | 6/2015 | Chaney et al. |
| 9,047,098 B2 | 6/2015 | Barten |
| 9,047,359 B2 | 6/2015 | Caballero et al. |
| 9,047,420 B2 | 6/2015 | Caballero |
| 9,047,525 B2 | 6/2015 | Barber |
| 9,047,531 B2 | 6/2015 | Showering et al. |
| 9,049,640 B2 | 6/2015 | Wang et al. |
| 9,053,055 B2 | 6/2015 | Caballero |
| 9,053,378 B1 | 6/2015 | Hou et al. |
| 9,053,380 B2 | 6/2015 | Xian et al. |
| 9,057,641 B2 | 6/2015 | Amundsen et al. |
| 9,058,526 B2 | 6/2015 | Powilleit |
| 9,064,165 B2 | 6/2015 | Havens et al. |
| 9,064,167 B2 | 6/2015 | Xian et al. |
| 9,064,168 B2 | 6/2015 | Todeschini et al. |
| 9,064,254 B2 | 6/2015 | Todeschini et al. |
| 9,066,032 B2 | 6/2015 | Wang |
| 9,070,032 B2 | 6/2015 | Corcoran |
| D734,339 S | 7/2015 | Zhou et al. |
| D734,751 S | 7/2015 | Oberpriller et al. |
| 9,082,023 B2 | 7/2015 | Feng et al. |
| 9,224,022 B2 | 12/2015 | Ackley et al. |
| 9,224,027 B2 | 12/2015 | Van Horn et al. |
| D747,321 S | 1/2016 | London et al. |
| 9,230,140 B1 | 1/2016 | Ackley |
| 9,443,123 B2 | 1/2016 | Hejl |
| 9,250,712 B1 | 2/2016 | Todeschini |
| 9,258,033 B2 | 2/2016 | Showering |
| 9,261,398 B2 | 2/2016 | Amundsen et al. |
| 9,262,633 B1 | 2/2016 | Todeschini et al. |
| 9,262,664 B2 | 2/2016 | Soule et al. |
| 9,274,806 B2 | 3/2016 | Barten |
| 9,282,501 B2 | 3/2016 | Wang et al. |
| 9,292,969 B2 | 3/2016 | Laffargue et al. |
| 9,298,667 B2 | 3/2016 | Caballero |
| 9,310,609 B2 | 4/2016 | Rueblinger et al. |
| 9,319,548 B2 | 4/2016 | Showering et al. |
| D757,009 S | 5/2016 | Oberpriller et al. |
| 9,342,724 B2 | 5/2016 | McCloskey |
| 9,342,827 B2 | 5/2016 | Smith |
| 9,355,294 B2 | 5/2016 | Smith et al. |
| 9,367,722 B2 | 6/2016 | Xian et al. |
| 9,375,945 B1 | 6/2016 | Bowles |
| D760,719 S | 7/2016 | Zhou et al. |
| 9,390,596 B1 | 7/2016 | Todeschini |
| 9,396,375 B2 | 7/2016 | Qu et al. |
| 9,398,008 B2 | 7/2016 | Todeschini et al. |
| D762,604 S | 8/2016 | Fitch et al. |
| D762,647 S | 8/2016 | Fitch et al. |
| 9,407,840 B2 | 8/2016 | Wang |
| 9,412,242 B2 | 8/2016 | Van Horn et al. |
| 9,418,252 B2 | 8/2016 | Nahill et al. |
| D766,244 S | 9/2016 | Zhou et al. |
| 9,443,222 B2 | 9/2016 | Singel et al. |
| 9,448,610 B2 | 9/2016 | Davis et al. |
| 9,478,113 B2 | 10/2016 | Xie et al. |
| 9,582,696 B2 | 2/2017 | Barber et al. |
| 9,616,749 B2 | 4/2017 | Chamberlin |
| 9,618,993 B2 | 4/2017 | Murawski et al. |
| 9,715,614 B2 | 7/2017 | Todeschini et al. |
| 9,734,493 B2 | 8/2017 | Gomez et al. |
| 10,019,334 B2 | 7/2018 | Caballero et al. |
| 10,021,043 B2 | 7/2018 | Sevier |
| 10,327,158 B2 | 6/2019 | Wang et al. |
| 10,387,962 B1* | 8/2019 | Potter .................. G06Q 40/08 |
| 10,410,029 B2 | 9/2019 | Powilleit |
| 2003/0093503 A1* | 5/2003 | Yamaki .................. G06F 19/00 709/220 |
| 2003/0163287 A1 | 8/2003 | Vock et al. |
| 2007/0063048 A1 | 3/2007 | Havens et al. |
| 2008/0097909 A1* | 4/2008 | Dicks .................... G06Q 50/22 705/50 |
| 2008/0174484 A1 | 7/2008 | Katz |
| 2009/0134221 A1 | 5/2009 | Zhu et al. |
| 2010/0177076 A1 | 7/2010 | Essinger et al. |
| 2010/0177080 A1 | 7/2010 | Essinger et al. |
| 2010/0177707 A1 | 7/2010 | Essinger et al. |
| 2010/0177749 A1 | 7/2010 | Essinger et al. |
| 2010/0265880 A1 | 10/2010 | Rautiola et al. |
| 2011/0169999 A1 | 7/2011 | Grunow et al. |
| 2011/0202554 A1 | 8/2011 | Powilleit et al. |
| 2012/0111946 A1 | 5/2012 | Golant |
| 2012/0168512 A1 | 7/2012 | Kotlarsky et al. |
| 2012/0193423 A1 | 8/2012 | Samek |
| 2012/0203647 A1 | 8/2012 | Smith |
| 2012/0223141 A1 | 9/2012 | Good et al. |
| 2013/0043312 A1 | 2/2013 | Van Horn |
| 2013/0075168 A1 | 3/2013 | Amundsen et al. |
| 2013/0175341 A1 | 7/2013 | Kearney et al. |
| 2013/0175343 A1 | 7/2013 | Good |
| 2013/0257744 A1 | 10/2013 | Daghigh et al. |
| 2013/0257759 A1 | 10/2013 | Daghigh |
| 2013/0270346 A1 | 10/2013 | Xian et al. |
| 2013/0287258 A1 | 10/2013 | Kearney |
| 2013/0292475 A1 | 11/2013 | Kotlarsky et al. |
| 2013/0292477 A1 | 11/2013 | Hennick et al. |
| 2013/0293539 A1 | 11/2013 | Hunt et al. |
| 2013/0293540 A1 | 11/2013 | Laffargue et al. |
| 2013/0306728 A1 | 11/2013 | Thuries et al. |
| 2013/0306731 A1 | 11/2013 | Pedraro |
| 2013/0307964 A1 | 11/2013 | Bremer et al. |

(56) References Cited

U.S. PATENT DOCUMENTS

| | | |
|---|---|---|
| 2013/0308625 A1 | 11/2013 | Park et al. |
| 2013/0313324 A1 | 11/2013 | Koziol et al. |
| 2013/0313325 A1 | 11/2013 | Wilz et al. |
| 2013/0335233 A1 | 12/2013 | Kamar et al. |
| 2013/0342717 A1 | 12/2013 | Havens et al. |
| 2014/0001267 A1 | 1/2014 | Giordano et al. |
| 2014/0002828 A1 | 1/2014 | Laffargue et al. |
| 2014/0008439 A1 | 1/2014 | Wang |
| 2014/0025584 A1 | 1/2014 | Liu et al. |
| 2014/0026188 A1* | 1/2014 | Gubler .................. H04W 12/08 726/3 |
| 2014/0100813 A1 | 1/2014 | Showering |
| 2014/0034734 A1 | 2/2014 | Sauerwein |
| 2014/0036848 A1 | 2/2014 | Pease et al. |
| 2014/0039693 A1 | 2/2014 | Havens et al. |
| 2014/0042814 A1 | 2/2014 | Kather et al. |
| 2014/0049120 A1 | 2/2014 | Kohtz et al. |
| 2014/0049635 A1 | 2/2014 | Laffargue et al. |
| 2014/0061306 A1 | 3/2014 | Wu et al. |
| 2014/0063289 A1 | 3/2014 | Hussey et al. |
| 2014/0066136 A1 | 3/2014 | Sauerwein et al. |
| 2014/0067692 A1 | 3/2014 | Ye et al. |
| 2014/0070005 A1 | 3/2014 | Nahill et al. |
| 2014/0071840 A1 | 3/2014 | Venancio |
| 2014/0074746 A1 | 3/2014 | Wang |
| 2014/0076974 A1 | 3/2014 | Havens et al. |
| 2014/0078341 A1 | 3/2014 | Havens et al. |
| 2014/0078342 A1 | 3/2014 | Li et al. |
| 2014/0078345 A1 | 3/2014 | Showering |
| 2014/0098792 A1 | 4/2014 | Wang et al. |
| 2014/0100774 A1 | 4/2014 | Showering |
| 2014/0103115 A1 | 4/2014 | Meier et al. |
| 2014/0104413 A1 | 4/2014 | McCloskey et al. |
| 2014/0104414 A1 | 4/2014 | McCloskey et al. |
| 2014/0104416 A1 | 4/2014 | Giordano et al. |
| 2014/0104451 A1 | 4/2014 | Todeschini et al. |
| 2014/0106594 A1 | 4/2014 | Skvoretz |
| 2014/0106725 A1 | 4/2014 | Sauerwein |
| 2014/0108010 A1 | 4/2014 | Maltseff et al. |
| 2014/0108402 A1 | 4/2014 | Gomez et al. |
| 2014/0108682 A1 | 4/2014 | Caballero |
| 2014/0110485 A1 | 4/2014 | Toa et al. |
| 2014/0114530 A1 | 4/2014 | Fitch et al. |
| 2014/0124577 A1 | 5/2014 | Wang et al. |
| 2014/0124579 A1 | 5/2014 | Ding |
| 2014/0125842 A1 | 5/2014 | Winegar |
| 2014/0125853 A1 | 5/2014 | Wang |
| 2014/0125999 A1 | 5/2014 | Longacre et al. |
| 2014/0129378 A1 | 5/2014 | Richardson |
| 2014/0131438 A1 | 5/2014 | Kearney |
| 2014/0131441 A1 | 5/2014 | Nahill et al. |
| 2014/0131443 A1 | 5/2014 | Smith |
| 2014/0131444 A1 | 5/2014 | Wang |
| 2014/0131445 A1 | 5/2014 | Ding et al. |
| 2014/0131448 A1 | 5/2014 | Xian et al. |
| 2014/0133379 A1 | 5/2014 | Wang et al. |
| 2014/0136208 A1 | 5/2014 | Maltseff et al. |
| 2014/0140585 A1 | 5/2014 | Wang |
| 2014/0151453 A1 | 6/2014 | Meier et al. |
| 2014/0152882 A1 | 6/2014 | Samek et al. |
| 2014/0158770 A1 | 6/2014 | Sevier et al. |
| 2014/0159869 A1 | 6/2014 | Zumsteg et al. |
| 2014/0166755 A1 | 6/2014 | Liu et al. |
| 2014/0166757 A1 | 6/2014 | Smith |
| 2014/0166759 A1 | 6/2014 | Liu et al. |
| 2014/0168787 A1 | 6/2014 | Wang et al. |
| 2014/0175165 A1 | 6/2014 | Havens et al. |
| 2014/0175172 A1 | 6/2014 | Jovanovski et al. |
| 2014/0191644 A1 | 7/2014 | Chaney |
| 2014/0191913 A1 | 7/2014 | Ge et al. |
| 2014/0197238 A1 | 7/2014 | Lui et al. |
| 2014/0197239 A1 | 7/2014 | Havens et al. |
| 2014/0197304 A1 | 7/2014 | Feng et al. |
| 2014/0203087 A1 | 7/2014 | Smith et al. |
| 2014/0204268 A1 | 7/2014 | Grunow et al. |
| 2014/0214631 A1 | 7/2014 | Hansen |
| 2014/0217166 A1 | 8/2014 | Berthiaume et al. |
| 2014/0217180 A1 | 8/2014 | Liu |
| 2014/0231500 A1 | 8/2014 | Ehrhart et al. |
| 2014/0232930 A1 | 8/2014 | Anderson |
| 2014/0247315 A1 | 9/2014 | Marty et al. |
| 2014/0263493 A1 | 9/2014 | Amurgis et al. |
| 2014/0263645 A1 | 9/2014 | Smith et al. |
| 2014/0267609 A1 | 9/2014 | Laffargue |
| 2014/0270196 A1 | 9/2014 | Braho et al. |
| 2014/0270229 A1 | 9/2014 | Braho |
| 2014/0278387 A1 | 9/2014 | DiGregorio |
| 2014/0278391 A1 | 9/2014 | Braho et al. |
| 2014/0282210 A1 | 9/2014 | Bianconi |
| 2014/0284384 A1 | 9/2014 | Lu et al. |
| 2014/0288933 A1 | 9/2014 | Braho et al. |
| 2014/0292564 A1 | 10/2014 | Park et al. |
| 2014/0297058 A1 | 10/2014 | Barker et al. |
| 2014/0299665 A1 | 10/2014 | Barber et al. |
| 2014/0312121 A1 | 10/2014 | Lu et al. |
| 2014/0319220 A1 | 10/2014 | Coyle |
| 2014/0319221 A1 | 10/2014 | Oberpriller et al. |
| 2014/0326787 A1 | 11/2014 | Barten |
| 2014/0332590 A1 | 11/2014 | Wang et al. |
| 2014/0344943 A1 | 11/2014 | Todeschini et al. |
| 2014/0346233 A1 | 11/2014 | Liu et al. |
| 2014/0351317 A1 | 11/2014 | Smith et al. |
| 2014/0353373 A1 | 12/2014 | Van Horn et al. |
| 2014/0361073 A1 | 12/2014 | Qu et al. |
| 2014/0361082 A1 | 12/2014 | Xian et al. |
| 2014/0362184 A1 | 12/2014 | Jovanovski et al. |
| 2014/0363015 A1 | 12/2014 | Braho |
| 2014/0369511 A1 | 12/2014 | Sheerin et al. |
| 2014/0374483 A1 | 12/2014 | Lu |
| 2014/0374485 A1 | 12/2014 | Xian et al. |
| 2015/0001301 A1 | 1/2015 | Ouyang |
| 2015/0001304 A1 | 1/2015 | Todeschini |
| 2015/0003673 A1 | 1/2015 | Fletcher |
| 2015/0009338 A1 | 1/2015 | Laffargue et al. |
| 2015/0009610 A1 | 1/2015 | London et al. |
| 2015/0014416 A1 | 1/2015 | Kotlarsky et al. |
| 2015/0021397 A1 | 1/2015 | Rueblinger et al. |
| 2015/0028102 A1 | 1/2015 | Ren et al. |
| 2015/0028103 A1 | 1/2015 | Jiang |
| 2015/0028104 A1 | 1/2015 | Ma et al. |
| 2015/0029002 A1 | 1/2015 | Yeakley et al. |
| 2015/0032709 A1 | 1/2015 | Maloy et al. |
| 2015/0039309 A1 | 2/2015 | Braho et al. |
| 2015/0040378 A1 | 2/2015 | Saber et al. |
| 2015/0048168 A1 | 2/2015 | Fritz et al. |
| 2015/0049347 A1 | 2/2015 | Laffargue et al. |
| 2015/0051992 A1 | 2/2015 | Smith |
| 2015/0053766 A1 | 2/2015 | Havens et al. |
| 2015/0053768 A1 | 2/2015 | Wang et al. |
| 2015/0053769 A1 | 2/2015 | Thuries et al. |
| 2015/0062366 A1 | 3/2015 | Liu et al. |
| 2015/0063215 A1 | 3/2015 | Wang |
| 2015/0063676 A1 | 3/2015 | Lloyd et al. |
| 2015/0069130 A1 | 3/2015 | Gannon |
| 2015/0071819 A1 | 3/2015 | Todeschini |
| 2015/0083800 A1 | 3/2015 | Li et al. |
| 2015/0086114 A1 | 3/2015 | Todeschini |
| 2015/0088522 A1 | 3/2015 | Hendrickson et al. |
| 2015/0096872 A1 | 4/2015 | Woodburn |
| 2015/0099557 A1 | 4/2015 | Pettinelli et al. |
| 2015/0100196 A1 | 4/2015 | Hollifield |
| 2015/0102109 A1 | 4/2015 | Huck |
| 2015/0115035 A1 | 4/2015 | Meier et al. |
| 2015/0127791 A1 | 5/2015 | Kosecki et al. |
| 2015/0128116 A1 | 5/2015 | Chen et al. |
| 2015/0129659 A1 | 5/2015 | Feng et al. |
| 2015/0133047 A1 | 5/2015 | Smith et al. |
| 2015/0134470 A1 | 5/2015 | Hejl et al. |
| 2015/0136851 A1 | 5/2015 | Harding et al. |
| 2015/0136854 A1 | 5/2015 | Lu et al. |
| 2015/0142492 A1 | 5/2015 | Kumar |
| 2015/0144692 A1 | 5/2015 | Hejl |
| 2015/0144698 A1 | 5/2015 | Teng et al. |
| 2015/0144701 A1 | 5/2015 | Xian et al. |

(56) References Cited

U.S. PATENT DOCUMENTS

| | | | |
|---|---|---|---|
| 2015/0149946 A1 | 5/2015 | Benos et al. | |
| 2015/0161429 A1 | 6/2015 | Xian | |
| 2015/0169925 A1 | 6/2015 | Chang et al. | |
| 2015/0169929 A1 | 6/2015 | Williams et al. | |
| 2015/0178523 A1 | 6/2015 | Gelay et al. | |
| 2015/0178534 A1 | 6/2015 | Jovanovski et al. | |
| 2015/0178535 A1 | 6/2015 | Bremer et al. | |
| 2015/0178536 A1 | 6/2015 | Hennick et al. | |
| 2015/0178537 A1 | 6/2015 | El et al. | |
| 2015/0181093 A1 | 6/2015 | Zhu et al. | |
| 2015/0181109 A1 | 6/2015 | Gillet et al. | |
| 2015/0186703 A1 | 7/2015 | Chen et al. | |
| 2015/0193644 A1 | 7/2015 | Kearney et al. | |
| 2015/0193645 A1 | 7/2015 | Colavito et al. | |
| 2015/0199957 A1 | 7/2015 | Funyak et al. | |
| 2015/0204671 A1 | 7/2015 | Showering | |
| 2015/0210199 A1 | 7/2015 | Payne | |
| 2015/0220753 A1 | 8/2015 | Zhu et al. | |
| 2015/0254485 A1 | 9/2015 | Feng et al. | |
| 2015/0327012 A1 | 11/2015 | Bian et al. | |
| 2016/0014251 A1 | 1/2016 | Hejl | |
| 2016/0040982 A1 | 2/2016 | Li et al. | |
| 2016/0042241 A1 | 2/2016 | Todeschini | |
| 2016/0057230 A1 | 2/2016 | Todeschini et al. | |
| 2016/0109219 A1 | 4/2016 | Ackley et al. | |
| 2016/0109220 A1 | 4/2016 | Laffargue | |
| 2016/0109224 A1 | 4/2016 | Thuries et al. | |
| 2016/0112631 A1 | 4/2016 | Ackley et al. | |
| 2016/0112643 A1 | 4/2016 | Laffargue et al. | |
| 2016/0124516 A1 | 5/2016 | Schoon et al. | |
| 2016/0125217 A1 | 5/2016 | Todeschini | |
| 2016/0125342 A1 | 5/2016 | Miller et al. | |
| 2016/0133253 A1 | 5/2016 | Braho et al. | |
| 2016/0171720 A1 | 6/2016 | Todeschini | |
| 2016/0171864 A1* | 6/2016 | Ciaramelletti | A42B 3/046 340/539.12 |
| 2016/0178479 A1 | 6/2016 | Goldsmith | |
| 2016/0180678 A1 | 6/2016 | Ackley et al. | |
| 2016/0189087 A1 | 6/2016 | Morton et al. | |
| 2016/0125873 A1 | 7/2016 | Braho et al. | |
| 2016/0227912 A1 | 8/2016 | Oberpriller et al. | |
| 2016/0232891 A1 | 8/2016 | Pecorari | |
| 2016/0292477 A1 | 10/2016 | Bidwell | |
| 2016/0294779 A1 | 10/2016 | Yeakley et al. | |
| 2016/0306769 A1 | 10/2016 | Kohtz et al. | |
| 2016/0314276 A1 | 10/2016 | Sewell et al. | |
| 2016/0314294 A1 | 10/2016 | Kubler et al. | |
| 2017/0055881 A1* | 3/2017 | Kang | A61B 5/002 |

FOREIGN PATENT DOCUMENTS

| | | | |
|---|---|---|---|
| WO | 2013163789 A1 | 11/2013 | |
| WO | 2013173985 A1 | 11/2013 | |
| WO | 2014019130 A1 | 2/2014 | |
| WO | 2014110495 A1 | 7/2014 | |

OTHER PUBLICATIONS

U.S. Appl. No. 29/525,068 for Tablet Computer With Removable Scanning Device filed Apr. 27, 2015 (Schulte et al.); 19 pages.
U.S. Appl. No. 29/468,118 for an Electronic Device Case, filed Sep. 26, 2013 (Oberpriller et al.); 44 pages.
U.S. Appl. No. 29/530,600 for Cyclone filed Jun. 18, 2015 (Vargo et al); 16 pages.
U.S. Appl. No. 14/707,123 for Application Independent DEX/UCS Interface filed May 8, 2015 (Pape); 47 pages.
U.S. Appl. No. 14/283,282 for Terminal Having Illumination and Focus Control filed May 21, 2014 (Liu et al.); 31 pages; now abandoned.
U.S. Appl. No. 14/705,407 for Method and System to Protect Software-Based Network-Connected Devices From Advanced Persistent Threat filed May 6, 2015 (Hussey et al.); 42 pages.
U.S. Appl. No. 14/704,050 for Intermediate Linear Positioning filed May 5, 2015 (Charpentier et al.); 60 pages.
U.S. Appl. No. 14/705,012 for Hands-Free Human Machine Interface Responsive to a Driver of a Vehicle filed May 6, 2015 (Fitch et al.); 44 pages.
U.S. Appl. No. 14/715,672 for Augumented Reality Enabled Hazard Display filed May 19, 2015 (Venkatesha et al.); 35 pages.
U.S. Appl. No. 14/735,717 for Indicia-Reading Systems Having an Interface With a User's Nervous System filed Jun. 10, 2015 (Todeschini); 39 pages.
U.S. Appl. No. 14/702,110 for System and Method for Regulating Barcode Data Injection Into a Running Application on a Smart Device filed May 1, 2015 (Todeschini et al.); 38 pages.
U.S. Appl. No. 14/747,197 for Optical Pattern Projector filed Jun. 23, 2015 (Thuries et al.); 33 pages.
U.S. Appl. No. 14/702,979 for Tracking Battery Conditions filed May 4, 2015 (Young et al.); 70 pages.
U.S. Appl. No. 29/529,441 for Indicia Reading Device filed Jun. 8, 2015 (Zhou et al.); 14 pages.
U.S. Appl. No. 14/747,490 for Dual-Projector Three-Dimensional Scanner filed Jun. 23, 2015 (Jovanovski et al.); 40 pages.
U.S. Appl. No. 14/740,320 for Tactile Switch for a Mobile Electronic Device filed Jun. 16, 2015 (Barndringa); 38 pages.
U.S. Appl. No. 14/740,373 for Calibrating a Volume Dimensioner filed Jun. 16, 2015 (Ackley et al.); 63 pages.
U.S. Appl. No. 13/367,978, filed Feb. 7, 2012, (Feng et al.); now abandoned.
U.S. Appl. No. 14/277,337 for Multipurpose Optical Reader, filed May 14, 2014 (Jovanovski et al.); 59 pages; now abandoned.
U.S. Appl. No. 14/446,391 for Multifunction Point of Sale Apparatus With Optical Signature Capture filed Jul. 30, 2014 (Good et al.); 37 pages; now abandoned.
U.S. Appl. No. 29/516,892 for Table Computer filed Feb. 6, 2015 (Bidwell et al.); 13 pages.
U.S. Appl. No. 29/523,098 for Handle for a Tablet Computer filed Apr. 7, 2015 (Bidwell et al.); 17 pages.
U.S. Appl. No. 29/528,890 for Mobile Computer Housing filed Jun. 2, 2015 (Fitch et al.); 61 pages.
U.S. Appl. No. 29/526,918 for Charging Base filed May 14, 2015 (Fitch et al.); 10 pages.
Search Report in related European Application No. 17154495.0 dated Aug. 18, 2017, pp. 1-12.
U.S. Patent Application for a Laser Scanning Module Employing an Elastomeric U-Hinge Based Laser Scanning Assembly, filed Feb. 7, 2012 (Feng et al.), U.S. Appl. No. 13/367,978.
U.S. Patent Application for Indicia Reader filed Apr. 1, 2015 (Huck), U.S. Appl. No. 14/676,109.

* cited by examiner

MONITORING USER BIOMETRIC PARAMETERS WITH NANOTECHNOLOGY IN PERSONAL LOCATOR BEACON

CROSS-REFERENCE TO RELATED APPLICATION

The present application claims the benefit of Indian Patent Application No. 201611009035 for Monitoring User Biometric Parameters with Nanotechnology in Personal Locator Beacon filed Mar. 15, 2016, which is hereby incorporated by reference in its entirety.

FIELD OF THE INVENTION

The invention is generally related to personal locator beacons, and, more specifically, to personal locator beacon systems that monitor user biometric parameters.

BACKGROUND

Personal tracker beacons are devices that track a user's geographic details, such as the user's latitude and longitude, using GPS satellite data. These beacons generally have a wireless transmitter that can be activated in life-threatening emergency situations to broadcast the user's geographic location to emergency personnel. The wireless transmitter can broadcast on a number of different frequencies, such as over local cellular networks, legacy analogue signal bands of 121.5 MHz or 243 MHz, or over the internationally designated 406 MHz digital radio-frequency band. The 406 MHz band has been designated an emergency band under the International Cospas-Sarsat Programme, which is an intergovernmental cooperative of 43 countries and agencies that maintains a network of satellites and ground facilities to receive distress signals from 406-MHz beacons and route the alerts to the proper authorities in more than 200 countries and territories. While geographical location information is critical in locating individuals in emergency situations, health data is not provided along with the location data. Thus, Search and Rescue teams responding to an emergency do not know the physical condition of the individual in distress, and must carry a general emergency kit that addresses a wide variety of situations. If the personal tracker beacon was equipped to provide health data on the individual in distress, Search and Rescue teams could tailor their emergency kits to better address the needs of the individual.

SUMMARY

In an aspect of the invention, a personal locator beacon system comprises: a personal locator beacon comprising a first microprocessor, a first global positioning subsystem coupled to the first microprocessor, a first low energy transceiver coupled to the first microprocessor, and a first low energy antennae coupled to the first low energy transceiver; and a biometrics monitor comprising a second microprocessor, a second low energy transceiver coupled to the second microprocessor, a second low energy antennae coupled to the second low energy transceiver, and one or more nanosensors.

In an embodiment, the first low energy transceiver, the first low energy antennae, the second low energy transceiver, and the second low energy antennae are low energy Bluetooth components.

In an embodiment, the personal locator beacon is communicatively coupled to the biometrics monitor through the first low energy transceiver and antennae and the second low energy transceiver and antennae.

In an embodiment, the nanosensor is a bioimpedance sensor configured to measure one or more of a user heart rate, respiration level, or hydration level.

In another embodiment, the nanosensor is an optical heart rate sensor.

In another embodiment, the nanosensor is a galvanic skin response sensor configured to monitor user sweat levels.

In another embodiment, the nanosensor is an accelerometer configured to count user steps or record sudden changes in movement.

In yet another embodiment, the nanosensor is a gyroscope configured to measure orientation of a user.

In yet another embodiment, the nanosensor is a thermometer configured to monitor user body temperature.

In another embodiment, the nanosensor is a radiation sensor configured to measure user radiation exposure.

In yet another embodiment, the radiation sensor measures user radiation exposure to ultra-violet, high-energy beta, gamma, x-ray frequencies, or any combination thereof.

In an embodiment, the nanosensor comprises a bioimpedance sensor, an optical heart rate sensor, a galvanic skin response sensor, an accelerometer, a gyroscope, a thermometer, ultra-violet radiation sensor, or any combination thereof.

In an embodiment, the biometrics monitor comprises a second GPS subsystem coupled to the second microprocessor.

In another embodiment, each of the first and second GPS subsystems comprise: a GPS receiver, a GPS antenna, and a GPS static memory communicatively coupled to the GPS receiver and configured to store: positioning information, time stamps associated with the positioning information, route information, speed of travel, or any combination thereof.

In an embodiment, the personal locator beacon comprising a beacon static memory communicatively coupled to the first microprocessor, being configured to receive and store nanosensor data for a period of configurable days.

In an embodiment, the biometrics monitor is a wearable device comprising a glove, a wristband, a necklace, a headband, a hat, smartphone, smartwatch or a chest strap.

In an embodiment, the biometrics monitor is a portable device carryable in a beltpack, backpack, or other external container.

In another aspect of the invention, a method of monitoring user biometric parameters in a personal locator beacon system, comprises: providing a personal locator beacon wirelessly coupled to a wearable biometrics monitor comprising one or more nanosensors; detecting a user biometric parameter of a user by the nanosensor; communicating the user biometric parameter from the biometric monitor to the personal locator beacon; and broadcasting from the personal locator beacon a distress signal comprising geographical location information and the user biometric parameter.

In an embodiment, the personal locator beacon comprises a GPS subsystem having: a GPS receiver, a GPS antenna, and a static memory coupled to the GPS receiver and configured to store positioning information and associated time stamps.

In another embodiment, the nanosensor comprises: a bioimpedance sensor configured to measure one or more user biometric parameters of a user heart rate, respiration level, or hydration level; an optical heart rate sensor configured to measure a user biometric parameter of a user heart rate; a galvanic skin response sensor configured to monitor a user biometric parameter of user sweat level; an accelerometer configured to measure a user biometric parameter of user steps or sudden changes in user movement; a gyroscope configured to measure a user biometric parameter of a user orientation; a thermometer configured to monitor a user biometric parameter of user body temperature; a radiation sensor configured to monitor user radiation exposure levels; or any combination thereof.

In another embodiment, the biometric monitor is a wearable device comprising a glove, a wristband, a necklace, a headband, a hat, smartphone, smartwatch, or a chest strap.

In an embodiment, the personal locator beacon is wirelessly coupled to the wearable biometric monitor using Bluetooth low energy.

In an embodiment, the user biometric parameters from the biometric monitor are communicated to the personal locator beacon at configured intervals.

In another embodiment, the configured intervals are event triggered intervals, predetermined fixed intervals, profile based intervals, or any combination thereof.

In an embodiment, the personal locator beacon is a Cospas-Sarsat distress beacon or a vehicle satcom relay.

BRIEF DESCRIPTION OF THE DRAWINGS

The invention will now be described by way of example, with reference to that accompanying Figures, of which.

DETAILED DESCRIPTION

All Cospas-Sarsat beacons are subject to the same radio-frequency specifications, but the beacons can be fashioned into a variety of mechanical structures. Additionally, the beacons can have a variety of disparate activation methods, the details of which are often tailored to different applications, and named accordingly: a) Emergency Position Indicating Radio Beacon ("EPIRB") for marine use; b) Emergency Locator Transmitter ("ELT") for aviation use; and c) Personal Locator Beacon ("PLB") for personal and/or terrestrial use. For the purpose of this invention, the term "PLB" will be generally used, along with "Locator Beacon", or "Beacon". Thus, "PLB" should not be interpreted in a restricted sense unless expressly stated, and will be understood to refer to any type of radio locator beacon (not necessarily restricted only to "personal").

Figure 1:
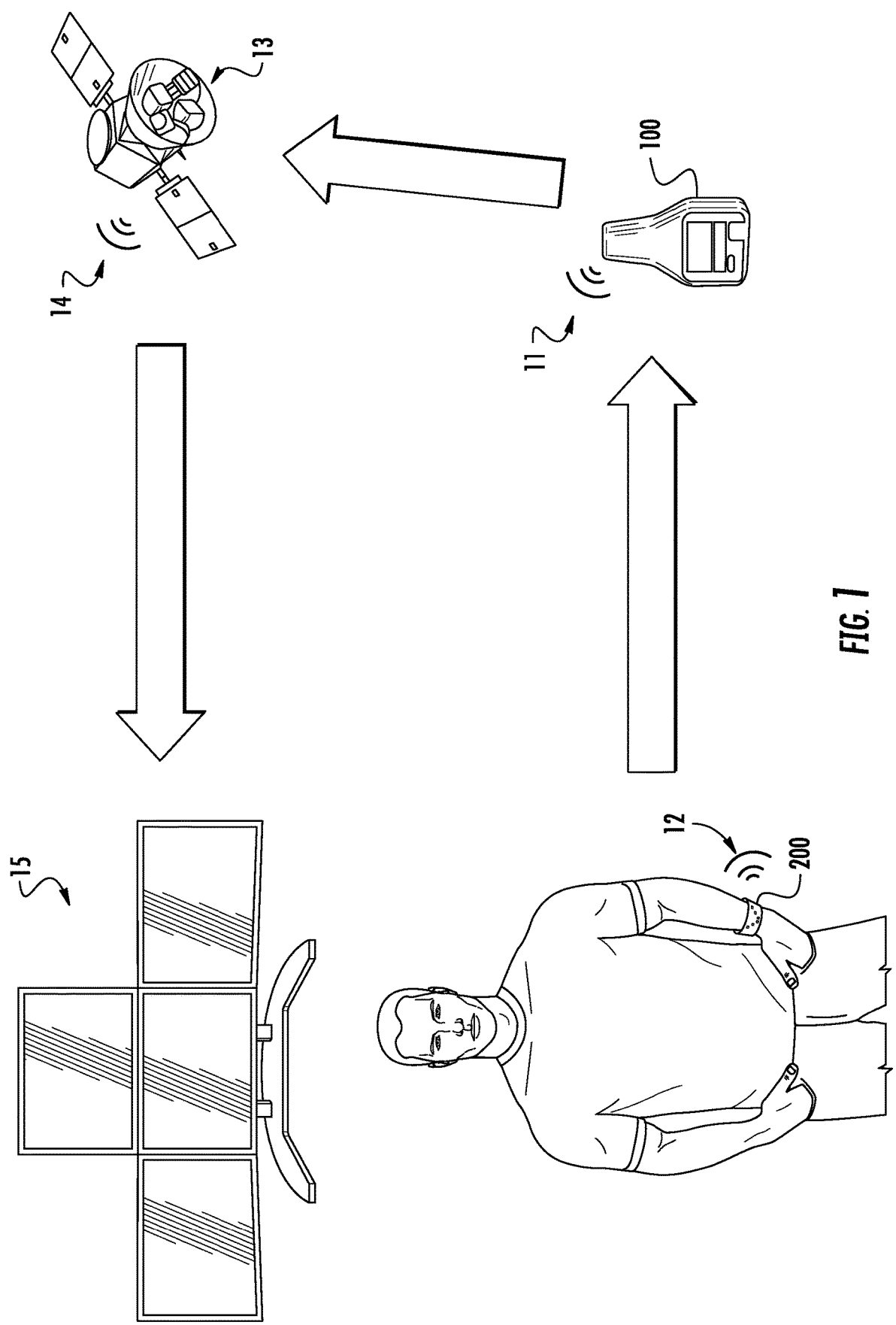
FIG. 1 is a perspective view of a personal locator beacon system.

In an embodiment shown in FIG. 1, a personal locator beacon system 1 includes a personal locator beacon 100 and biometrics monitor 200.

Figure 2:
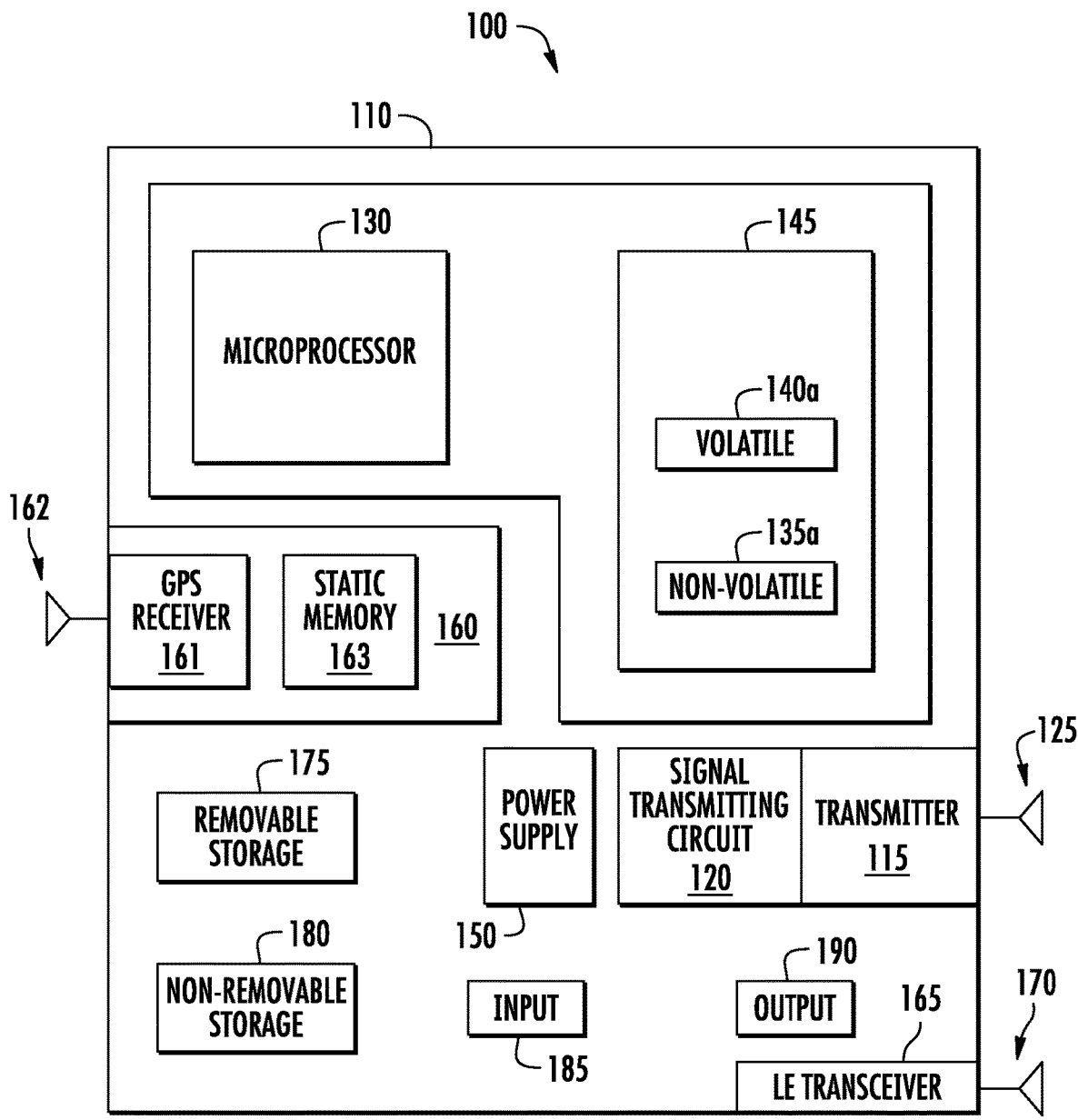
FIG. 2 is a schematic diagram of the personal locator beacon.

In an embodiment shown in FIG. 2, the personal locator beacon 100 includes a housing 110 having one or more of a radio frequency transmitter 115, signal transmitting circuit 120, first radio frequency antenna 125, first microprocessor 130, first memory 145, power supply 150, first global positioning system ("GPS") subsystem 160, first low energy transceiver 165, and a first low energy antenna 170.

As shown in the embodiment of FIG. 2, the housing 110 houses the various components of the personal locator beacon 100, and can be any variety of shapes or sizes, depending on the application (e.g. a user worn, vehicle mounted, etc.). The housing 110 can be made of a thermoset or thermoplastic material, metal, composite material, or any combination thereof.

The radio frequency transmitter 115 is electrically connected to the first radio frequency antenna 125 and the signal transmitting circuit 120. The signal transmitting circuit 120 is electrically connected to the first microprocessor 130. The first microprocessor 130 sends radio transmission instructions to the radio frequency transmitter 115 via the signal transmitting circuit 120. The radio frequency transmitter 115 sends signals to the first radio frequency antenna 125 to be transmitted by the first radio frequency antenna 125 on domestic or internationally recognized radio-frequency distress bands. In an embodiment, the first radio frequency antenna 125 transmits signals at approximately 406 MHz. In another embodiment, the first radio frequency antenna 125 transmits signals at approximately 121.5 MHz. In another embodiment, the first radio frequency antenna 125 transmits signals at approximately 243 MHz. In another embodiment, the first radio frequency antenna 125 transmits signals at a frequency corresponding to local cellular phone networks, such as 700 MHz, 800 MHz, 850 MHz, 1700 MHz, 1900 MHz, or any other commonly used cellular phone frequencies used by cellular phone networks. In an embodiment (not shown), the personal locator beacon 100 includes one or more microprocessors 130 connected to transmitting signal circuit. Those of ordinary skill in the art would appreciate that in an embodiment, the radio frequency transmitter 115 can transmit on two or more of the above described frequency bands. In an embodiment, the radio frequency transmitter 115 is a transceiver.

In an embodiment shown in FIG. 2, first memory 145 can include volatile memory (e.g. RAM) 140a and non-volatile memory 135a (e.g. ROM) electrically connected to first microprocessor 130. Personal locator beacon 100 can include—or have access to a computing environment that includes—a variety of computer-readable media, such as the volatile memory 140a and non-volatile memory 135a, a removable storage 175, and non-removable storage 180. First memory 145 storage includes the random access memory (RAM) 140 and read only memory (ROM) 135, as well as erasable programmable read-only memory (EPROM), electrically erasable programmable read-only memory (EEPROM), flash memory or other memory technologies, compact disc read-only memory (CD ROM), Digital Versatile Disks (DVD) or other optical disk storage, magnetic cassettes, magnetic tape, magnetic disk storage or other magnetic storage devices, or any other medium capable of storing computer-readable instructions.

Personal locator beacon 100 can include or have access to a computing environment that includes input 185 and/or output 190. Output 190 can include a display device, such as a touchscreen, that also can serve as an input device. The input 185 can include one or more of a touchscreen, touchpad, mouse, keyboard, camera, one or more device-specific buttons, one or more sensors integrated within or coupled via wired or wireless data connections to the personal locator beacon 100, and other input devices.

Computer-readable instructions are stored on a computer-readable medium, such as the first memory 145, and are executable by the first microprocessor 130.

In an embodiment shown in FIG. 2, a power supply 150 provides power to the components of the personal locator beacon 100. An example of the power supply 150 is a battery, although other sources of power could also provide the requisite power to the components of the personal locator beacon 100.

In an embodiment shown in FIG. 2, the first GPS subsystem 160 includes a GPS receiver 161, GPS antenna 162, and a GPS static memory 163. The GPS receiver 161 is electrically connected to the first microprocessor 130, GPS antenna 162, and GPS static memory 163. The GPS receiver 161 receives and processes signals from positional satellites via the GPS antenna 162. Generally, the processed signals are positioning information and associated time stamps. In turn, the GPS receiver 161 sends the processed signals to the GPS static memory 163, which stores current and/or past positioning information and associated time stamps. The GPS static memory 163 is electrically connected to the first microprocessor 130, and the stored current and/or past positioning information and associated time stamps can be accessed by the first microprocessor 130, which in turn, can send this information for storage in memory 135,140,145, and/or can be sent to signal transmitting circuit 120 upon PLB 100 activation. Additionally, in an embodiment the GPS static memory 163 can store route information and speed of travel for a user based on the current and past positioning information and associated time stamps, and this information can also be accessed by the first microprocessor 130

As shown in the embodiment of FIG. 2, the first low energy transceiver 165 is electrically connected to the first low energy antenna 170 and to the first microprocessor 130. In an embodiment the first low energy transceiver 165 and first low energy antenna 170 are low energy Bluetooth components. The first low energy transceiver 165 receives signals detected by the first low energy antenna 170 and sends the signals to the first microprocessor 130. Additionally the first low energy transceiver 165 receives signals from the first microprocessor 130, and broadcasts those signals via the first low energy antenna 170.

Figure 3:
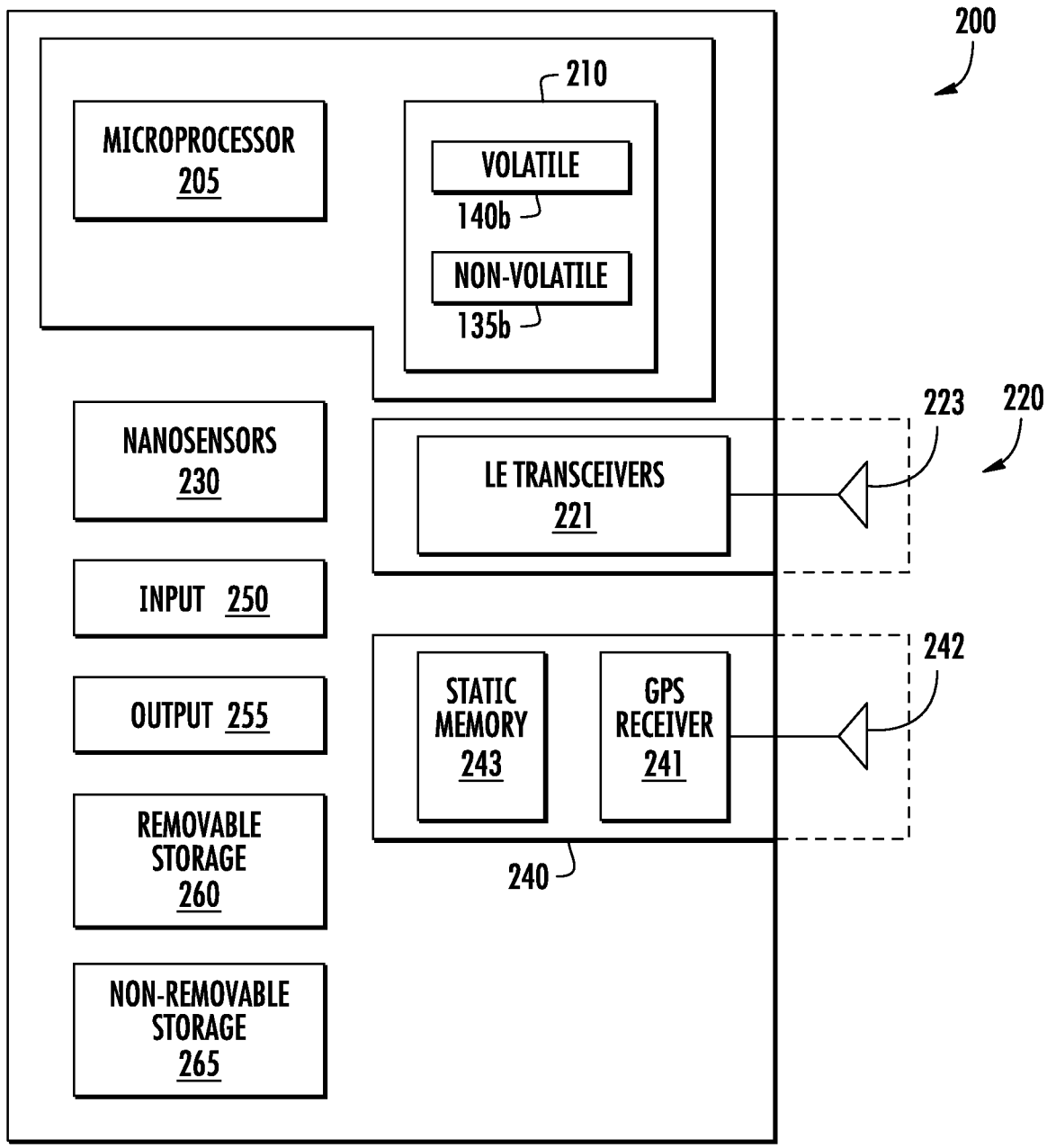
FIG. 3 is a schematic diagram of the biometrics monitor.

In an embodiment shown in FIG. 3, the biometrics monitor 200 is a user-wearable device that includes a second microprocessor 205, second memory 210, wireless communication system 220, and one or more nanosensors 230. The biometrics monitor 200 can be fashioned in many forms, including a glove, wristband, necklace, headband, hat, chest strap, or any other wearable device. In an embodiment, the biometrics monitor 200 is a smartphone, smartwatch, or fitness band having a one or more biometric nanosensors 230.

The term biometric nanosensor referred to herein is any biometric sensor sufficiently small in size and weight to be suitable for personal use. By way of non-limiting example, biometric nanosensors can include, but are not limited to, biometric sensors positioned in devices that can be carried in a backpack, beltpack/fannypack, or similar user-carryable housing; biometric sensors in wearable devices, as discussed further herein; and biometric sensors that may be injected, implanted, or otherwise carried inside the body. In addition, the biometric nanosensors can be contained in or associated with devices having significant functionality in addition to monitoring or measurement of biometrics, such as smartphones, smartwatches, or in devices whose primary or sole functionality consists of monitoring or measurement of biometrics, such as commercially available fitness bands.

The second microprocessor 205 is electrically connected to the second memory 210, wireless communication system 220, and to one or more of the nanosensors 230.

The second microprocessor 205 is substantially similar in function and structure to the first microprocessor 130, and the second memory 210 is substantially similar to the first memory 145.

In an embodiment shown in FIG. 3, second memory 210 can include volatile memory (e.g. RAM) 140b and non-volatile memory 135b (e.g. ROM) electrically connected to second microprocessor 205. Biometrics monitor 200 can include—or have access to a computing environment that includes—a variety of computer-readable media, such as the volatile memory 140b and non-volatile memory 135b, a removable storage 260, and non-removable storage 265. Second memory 210 storage includes the random access memory (RAM) 140b and read only memory (ROM) 135b, as well as erasable programmable read-only memory (EPROM), electrically erasable programmable read-only memory (EEPROM), flash memory (e.g. solid state drives), or other memory technologies, Biometrics monitor 200 can include or have access to a computing environment that includes input 250 and/or output 255. Output 255 can include a display device, such as a touchscreen, that also can serve as an input device. The input 250 can include one or more of a touchscreen, touchpad, mouse, keyboard, camera, one or more device-specific buttons, one or more sensors integrated within or coupled via wired or wireless data connections to the biometrics monitor 200, and other input devices.

Computer-readable instructions are stored on a computer-readable medium such as the second memory 210, and are executable by the second microprocessor 205.

The wireless communication system 220 includes a second low energy (LE) transceiver 221 communicatively coupled to the second microprocessor 205, and a second low energy (LE) antenna 223 electrically coupled to the second low energy (LE) transceiver 221. In an embodiment, the second low energy transceiver 221 and second low energy antenna 223 are low energy Bluetooth components. The second low energy transceiver 221 receives signals from the second low energy antenna 223 and sends the signals to the second microprocessor 205. Additionally the second low energy transceiver 221 receives signals from the second microprocessor 205, and broadcasts those signals using the second low energy antenna 223.

Figure 4:
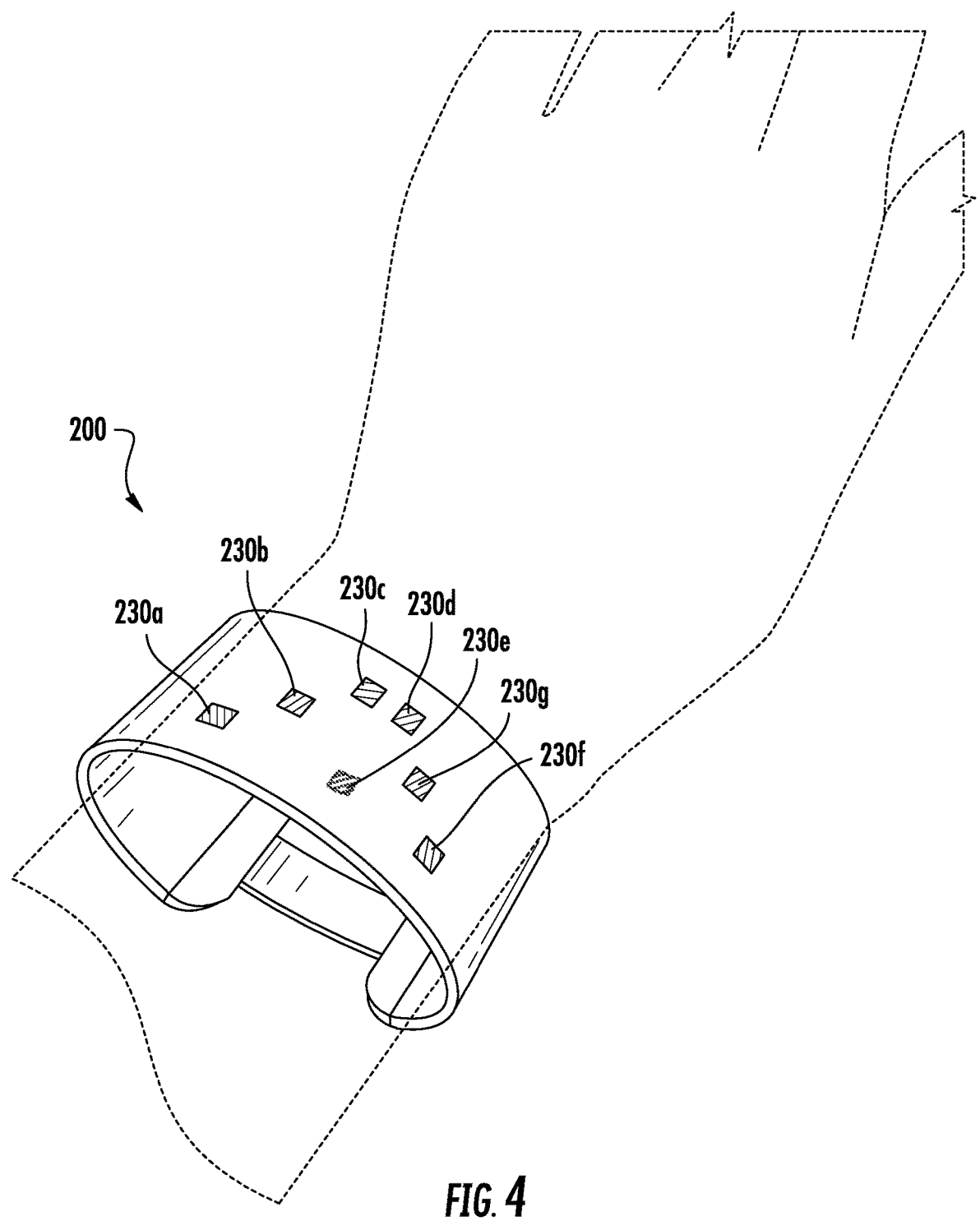
FIG. 4 is a perspective view of a biometrics monitor.

As shown in FIG. 4, the nanosensor 230 is a biometric reading device. In an embodiment, the nanosensor 230 can be one or more of a bioimpedance sensor 230a, an optical heart rate sensor 230b, a galvanic skin response sensor 230c, an accelerometer 230d, a gyroscope 230e, a thermometer 230f, radiation sensor 230g, or any combination thereof. In an embodiment, the bioimpedance sensor 230a is configured to measure one or more of a user heart rate, respiration level, or hydration level. In an embodiment, the optical heart rate sensor 230b measure user heart rate by using a light sensor that detects minor fluctuations in the user's capillaries. In an embodiment, the galvanic skin response sensor 230c is configured to monitor user sweat levels by measuring electrical conductance of the user's skin. In an embodiment, the accelerometer 230d is configured to count user steps or record sudden changes in movement. In an embodiment, the gyroscope 230e is configured to measure orientation of a user. In an embodiment, thermometer 230f is configured to monitor user body temperature. In an embodiment, the radiation sensor 230g is a radiation dosimeter configured to monitor levels of user ultra-violet (UV), high-energy beta, gamma, and/or x-ray radiation exposure.

Each nanosensor 230a-g is electrically connected to the second microprocessor 205, and each sends biometric information to the microprocessor 205. The microprocessor 205 can store the biometric information in the second memory 210, and/or send the biometric information to the wireless communication system 220.

In an embodiment, the biometrics monitor 200 includes a second GPS subsystem 240. Similar to the first GPS subsystem 160, the second GPS subsystem 240 includes a GPS receiver 241, GPS antenna 242, and a GPS static memory 243. The GPS receiver 241 is electrically connected to the second microprocessor 205, GPS antenna 242, and GPS static memory 243. The GPS antenna 242 receives signals from global positioning satellites, which in turn, are then sent to the GPS receiver 241. The GPS receiver 241 sends the signals to the GPS static memory 243, which stores current and/or past positioning information and associated time stamps. The GPS receiver 241 can transmit this current and/or past positioning information and associated time stamps to the second microprocessor 205, which in turn, can send this information to be stored in the second memory 210, and/or can be sent to second low energy transceiver 221 upon PLB 100 activation. Additionally, in an embodiment the GPS static memory 243 can store route information and speed of travel for a user based on the current and past positioning information and associated time stamps, and this information can also be accessed by the second microprocessor 205.

As shown in the embodiment of FIG. 1, the personal locator beacon 100 is communicatively coupled to the biometrics monitor 200. In an embodiment, the personal locator beacon 100 is communicatively coupled to the biometrics monitor 200 through the first low energy transceiver 165 and first low energy antennae 170, and the second low energy transceiver 221 and second low energy antennae 223. The biometric monitor 200 sends biometric parameters collected from the nanosensors 230a-g to the personal locator beacon 100 using low energy Bluetooth signals at configured intervals. The configured intervals can be an event triggered intervals (e.g. activation of personal locator beacon 100 to broadcast distress signal 11), predetermined fixed intervals (e.g. user configured times), profile based intervals (e.g. schedule or activity specific times), or any combination thereof.

In an embodiment, the biometrics monitor 200 sends user geographical information collected from the second GPS subsystem 240 to the personal locator beacon 100, either individually, or in combination with the biometric parameters collected from the nanosensors 230a-g. The user geographical information can be sent to the personal locator beacon 100 at the configured intervals.

In an embodiment, the biometrics monitor 200 can include an identification serial number unique to the biometric monitor 200. The identification serial number can be sent to the personal locator beacon 100 at the same or different time the biometric parameters and/or user geographical information is sent from the biometric monitor 200 to the personal locator beacon 100.

In an embodiment, the personal locator beacon system 1 can included two or more biometrics monitors 200, each of which can be worn by a different user. Each biometrics monitor 200 would include an identification serial number unique to that biometric monitor 100, and each of the biometric monitors 200 can send its identification serial number to the personal locator beacon 100 at the same or different time the biometric parameters and/or user geographical information is sent from each biometric monitor 200 to the personal locator beacon 100.

As generally shown in the embodiment of FIG. 1, when the personal locator beacon 100 has been activated to broadcast a distress signal 11 using the radio frequency transmitter 115 via the first radio frequency antenna 125, the distress signal includes geographical coordinates determined by the first GPS subsystem 160. In another embodiment, the distress signal 11 would include both the geographical coordinates from the first GPS subsystem 160 and biometric parameters received from one or more nanosensors 230. In another embodiment, the distress signal 11 would include the geographical coordinates from the first GPS subsystem 160 and the user geographical coordinates received from the second GPS subsystem 240. In yet another embodiment, the distress signal 11 would include the geographical coordinates from the first GPS subsystem 160, the user geographical coordinates received from the second GPS subsystem 240, and the biometric parameters received from one or more nanosensors 230. In another embodiment, the distress signal 11 can include geographical coordinates from the first GPS subsystem 160, user geographical coordinates received from the second GPS subsystem 240, biometric parameters received from one or more nanosensors 230, identification serial number of the biometric monitor 200, or any combination thereof.

Thus, as generally shown in the embodiment of FIG. 1, the biometrics monitor 200 broadcasts a biometrics containing signal 12 to the personal locator beacon 100. The personal locator beacon 100 in turn, broadcasts the distress signal 11 which is detected by either ground-based or satellite-based communication systems 13. These communication systems 13 then relay 14 the information contained in the distress signal 11 to the appropriate emergency responders 15.

By including additional geographical and biometric parameter information in the distress signal 11, emergency responders 15 will be alerted to both the exact geographical location of the user, as well as the general health condition of the user before embarking on the rescue mission. Thus, it is possible for the emergency responders 15 to gear up with emergency equipment that fits the user's situation.

Figure 5:
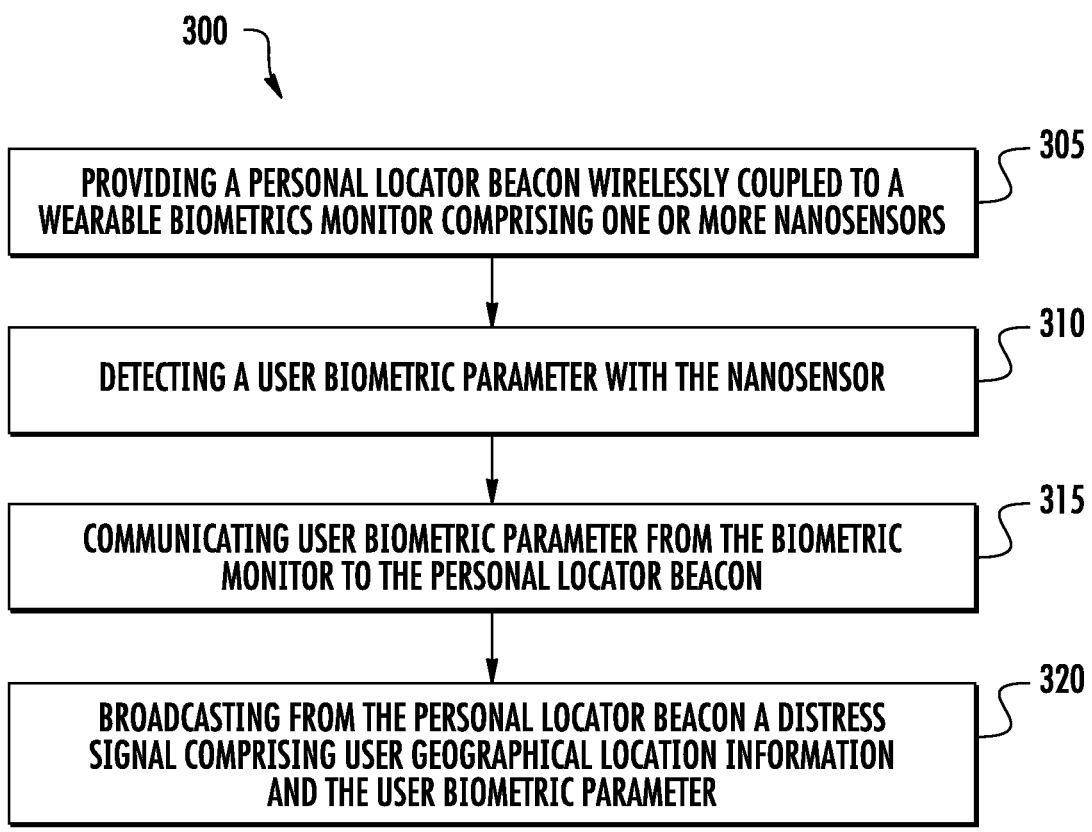
FIG. 5 is a flow diagram of a method of monitoring biometrics parameters in the personal locator beacon system.

In an embodiment shown in FIG. 5, a method 300 of monitoring biometrics parameters in the personal locator beacon system 1 comprises providing a personal locator beacon 100 wirelessly coupled to a wearable biometrics monitor 200 having one or more nanosensors 230 at block 305; detecting a user biometric parameter by the nanosensor 230 at block 310; communicating user biometric parameter from the biometric monitor 200 to the personal locator beacon 100 at block 315; and broadcasting from the personal locator beacon 100 a distress signal 11 comprising geographical location information and the user biometric parameter at block 320.

In an embodiment, the biometric parameters from the biometric monitor are communicated to the personal locator beacon 100 at configured intervals. The configured intervals can be event triggered intervals (e.g. when the personal locator beacon is manually or automatically activated), predetermined fixed intervals set by the user or manufacturer, user profile based intervals (e.g. based on the particular activity such as remote lone worker or adventure tourist; working environment of the user; or employer duty of care), or any combination thereof.

In an embodiment, the personal locator beacon 100 is a Cospas Sarsat distress beacon or a vehicle satcom relay.

To supplement the present disclosure, this application incorporates entirely by reference the following patents, patent application publications, and patent applications:

U.S. Pat. Nos. 6,832,725; 7,128,266;
U.S. Pat. Nos. 7,159,783; 7,413,127;
U.S. Pat. Nos. 7,726,575; 8,294,969;
U.S. Pat. Nos. 8,317,105; 8,322,622;
U.S. Pat. Nos. 8,366,005; 8,371,507;
U.S. Pat. Nos. 8,376,233; 8,381,979;
U.S. Pat. Nos. 8,390,909; 8,408,464;
U.S. Pat. Nos. 8,408,468; 8,408,469;
U.S. Pat. Nos. 8,424,768; 8,448,863;
U.S. Pat. Nos. 8,457,013; 8,459,557;
U.S. Pat. Nos. 8,469,272; 8,474,712;
U.S. Pat. Nos. 8,479,992; 8,490,877;
U.S. Pat. Nos. 8,517,271; 8,523,076;
U.S. Pat. Nos. 8,528,818; 8,544,737;
U.S. Pat. Nos. 8,548,242; 8,548,420;
U.S. Pat. Nos. 8,550,335; 8,550,354;
U.S. Pat. Nos. 8,550,357; 8,556,174;
U.S. Pat. Nos. 8,556,176; 8,556,177;
U.S. Pat. Nos. 8,559,767; 8,599,957;
U.S. Pat. Nos. 8,561,895; 8,561,903;
U.S. Pat. Nos. 8,561,905; 8,565,107;
U.S. Pat. Nos. 8,571,307; 8,579,200;
U.S. Pat. Nos. 8,583,924; 8,584,945;
U.S. Pat. Nos. 8,587,595; 8,587,697;
U.S. Pat. Nos. 8,588,869; 8,590,789;
U.S. Pat. Nos. 8,596,539; 8,596,542;
U.S. Pat. Nos. 8,596,543; 8,599,271;
U.S. Pat. Nos. 8,599,957; 8,600,158;
U.S. Pat. Nos. 8,600,167; 8,602,309;
U.S. Pat. Nos. 8,608,053; 8,608,071;
U.S. Pat. Nos. 8,611,309; 8,615,487;
U.S. Pat. Nos. 8,616,454; 8,621,123;
U.S. Pat. Nos. 8,622,303; 8,628,013;
U.S. Pat. Nos. 8,628,015; 8,628,016;
U.S. Pat. Nos. 8,629,926; 8,630,491;
U.S. Pat. Nos. 8,635,309; 8,636,200;
U.S. Pat. Nos. 8,636,212; 8,636,215;
U.S. Pat. Nos. 8,636,224; 8,638,806;
U.S. Pat. Nos. 8,640,958; 8,640,960;
U.S. Pat. Nos. 8,643,717; 8,646,692;
U.S. Pat. Nos. 8,646,694; 8,657,200;
U.S. Pat. Nos. 8,659,397; 8,668,149;
U.S. Pat. Nos. 8,678,285; 8,678,286;
U.S. Pat. Nos. 8,682,077; 8,687,282;
U.S. Pat. Nos. 8,692,927; 8,695,880;
U.S. Pat. Nos. 8,698,949; 8,717,494;
U.S. Pat. Nos. 8,717,494; 8,720,783;
U.S. Pat. Nos. 8,723,804; 8,723,904;
U.S. Pat. No. 8,727,223; U.S. Pat. No. D702,237;
U.S. Pat. Nos. 8,740,082; 8,740,085;
U.S. Pat. Nos. 8,746,563; 8,750,445;
U.S. Pat. Nos. 8,752,766; 8,756,059;
U.S. Pat. Nos. 8,757,495; 8,760,563;
U.S. Pat. Nos. 8,763,909; 8,777,108;
U.S. Pat. Nos. 8,777,109; 8,779,898;
U.S. Pat. Nos. 8,781,520; 8,783,573;
U.S. Pat. Nos. 8,789,757; 8,789,758;
U.S. Pat. Nos. 8,789,759; 8,794,520;
U.S. Pat. Nos. 8,794,522; 8,794,525;
U.S. Pat. Nos. 8,794,526; 8,798,367;
U.S. Pat. Nos. 8,807,431; 8,807,432;
U.S. Pat. Nos. 8,820,630; 8,822,848;
U.S. Pat. Nos. 8,824,692; 8,824,696;
U.S. Pat. Nos. 8,842,849; 8,844,822;
U.S. Pat. Nos. 8,844,823; 8,849,019;
U.S. Pat. Nos. 8,851,383; 8,854,633;
U.S. Pat. Nos. 8,866,963; 8,868,421;
U.S. Pat. Nos. 8,868,519; 8,868,802;
U.S. Pat. Nos. 8,868,803; 8,870,074;
U.S. Pat. Nos. 8,879,639; 8,880,426;
U.S. Pat. Nos. 8,881,983; 8,881,987;
U.S. Pat. Nos. 8,903,172; 8,908,995;
U.S. Pat. Nos. 8,910,870; 8,910,875;
U.S. Pat. Nos. 8,914,290; 8,914,788;
U.S. Pat. Nos. 8,915,439; 8,915,444;
U.S. Pat. Nos. 8,916,789; 8,918,250;
U.S. Pat. Nos. 8,918,564; 8,925,818;
U.S. Pat. Nos. 8,939,374; 8,942,480;
U.S. Pat. Nos. 8,944,313; 8,944,327;
U.S. Pat. Nos. 8,944,332; 8,950,678;
U.S. Pat. Nos. 8,967,468; 8,971,346;
U.S. Pat. Nos. 8,976,030; 8,976,368;
U.S. Pat. Nos. 8,978,981; 8,978,983;
U.S. Pat. Nos. 8,978,984; 8,985,456;
U.S. Pat. Nos. 8,985,457; 8,985,459;
U.S. Pat. Nos. 8,985,461; 8,988,578;
U.S. Pat. Nos. 8,988,590; 8,991,704;
U.S. Pat. Nos. 8,996,194; 8,996,384;
U.S. Pat. Nos. 9,002,641; 9,007,368;
U.S. Pat. Nos. 9,010,641; 9,015,513;
U.S. Pat. Nos. 9,016,576; 9,022,288;
U.S. Pat. Nos. 9,030,964; 9,033,240;
U.S. Pat. Nos. 9,033,242; 9,036,054;
U.S. Pat. Nos. 9,037,344; 9,038,911;
U.S. Pat. Nos. 9,038,915; 9,047,098;
U.S. Pat. Nos. 9,047,359; 9,047,420;
U.S. Pat. Nos. 9,047,525; 9,047,531;
U.S. Pat. Nos. 9,053,055; 9,053,378;
U.S. Pat. Nos. 9,053,380; 9,058,526;
U.S. Pat. Nos. 9,064,165; 9,064,167;
U.S. Pat. Nos. 9,064,168; 9,064,254;
U.S. Pat. Nos. 9,066,032; 9,070,032;
U.S. Design Pat. No. D716,285;
U.S. Design Pat. No. D723,560;
U.S. Design Pat. No. D730,357;
U.S. Design Pat. No. D730,901;
U.S. Design Pat. No. D730,902;
U.S. Design Pat. No. D733,112;
U.S. Design Pat. No. D734,339;
International Publication No. 2013/163789;
International Publication No. 2013/173985;
International Publication No. 2014/019130;
International Publication No. 2014/110495;
U.S. Patent Application Publication No. 2008/0185432;
U.S. Patent Application Publication No. 2009/0134221;
U.S. Patent Application Publication No. 2010/0177080;
U.S. Patent Application Publication No. 2010/0177076;
U.S. Patent Application Publication No. 2010/0177707;
U.S. Patent Application Publication No. 2010/0177749;
U.S. Patent Application Publication No. 2010/0265880;
U.S. Patent Application Publication No. 2011/0202554;
U.S. Patent Application Publication No. 2012/0111946;
U.S. Patent Application Publication No. 2012/0168511;
U.S. Patent Application Publication No. 2012/0168512;
U.S. Patent Application Publication No. 2012/0193423;
U.S. Patent Application Publication No. 2012/0203647;
U.S. Patent Application Publication No. 2012/0223141;
U.S. Patent Application Publication No. 2012/0228382;
U.S. Patent Application Publication No. 2012/0248188;
U.S. Patent Application Publication No. 2013/0043312;
U.S. Patent Application Publication No. 2013/0082104;
U.S. Patent Application Publication No. 2013/0175341;
U.S. Patent Application Publication No. 2013/0175343;
U.S. Patent Application Publication No. 2013/0257744;

U.S. Patent Application Publication No. 2013/0257759;
U.S. Patent Application Publication No. 2013/0270346;
U.S. Patent Application Publication No. 2013/0287258;
U.S. Patent Application Publication No. 2013/0292475;
U.S. Patent Application Publication No. 2013/0292477;
U.S. Patent Application Publication No. 2013/0293539;
U.S. Patent Application Publication No. 2013/0293540;
U.S. Patent Application Publication No. 2013/0306728;
U.S. Patent Application Publication No. 2013/0306731;
U.S. Patent Application Publication No. 2013/0307964;
U.S. Patent Application Publication No. 2013/0308625;
U.S. Patent Application Publication No. 2013/0313324;
U.S. Patent Application Publication No. 2013/0313325;
U.S. Patent Application Publication No. 2013/0342717;
U.S. Patent Application Publication No. 2014/0001267;
U.S. Patent Application Publication No. 2014/0008439;
U.S. Patent Application Publication No. 2014/0025584;
U.S. Patent Application Publication No. 2014/0034734;
U.S. Patent Application Publication No. 2014/0036848;
U.S. Patent Application Publication No. 2014/0039693;
U.S. Patent Application Publication No. 2014/0042814;
U.S. Patent Application Publication No. 2014/0049120;
U.S. Patent Application Publication No. 2014/0049635;
U.S. Patent Application Publication No. 2014/0061306;
U.S. Patent Application Publication No. 2014/0063289;
U.S. Patent Application Publication No. 2014/0066136;
U.S. Patent Application Publication No. 2014/0067692;
U.S. Patent Application Publication No. 2014/0070005;
U.S. Patent Application Publication No. 2014/0071840;
U.S. Patent Application Publication No. 2014/0074746;
U.S. Patent Application Publication No. 2014/0076974;
U.S. Patent Application Publication No. 2014/0078341;
U.S. Patent Application Publication No. 2014/0078345;
U.S. Patent Application Publication No. 2014/0097249;
U.S. Patent Application Publication No. 2014/0098792;
U.S. Patent Application Publication No. 2014/0100813;
U.S. Patent Application Publication No. 2014/0103115;
U.S. Patent Application Publication No. 2014/0104413;
U.S. Patent Application Publication No. 2014/0104414;
U.S. Patent Application Publication No. 2014/0104416;
U.S. Patent Application Publication No. 2014/0104451;
U.S. Patent Application Publication No. 2014/0106594;
U.S. Patent Application Publication No. 2014/0106725;
U.S. Patent Application Publication No. 2014/0108010;
U.S. Patent Application Publication No. 2014/0108402;
U.S. Patent Application Publication No. 2014/0110485;
U.S. Patent Application Publication No. 2014/0114530;
U.S. Patent Application Publication No. 2014/0124577;
U.S. Patent Application Publication No. 2014/0124579;
U.S. Patent Application Publication No. 2014/0125842;
U.S. Patent Application Publication No. 2014/0125853;
U.S. Patent Application Publication No. 2014/0125999;
U.S. Patent Application Publication No. 2014/0129378;
U.S. Patent Application Publication No. 2014/0131438;
U.S. Patent Application Publication No. 2014/0131441;
U.S. Patent Application Publication No. 2014/0131443;
U.S. Patent Application Publication No. 2014/0131444;
U.S. Patent Application Publication No. 2014/0131445;
U.S. Patent Application Publication No. 2014/0131448;
U.S. Patent Application Publication No. 2014/0133379;
U.S. Patent Application Publication No. 2014/0136208;
U.S. Patent Application Publication No. 2014/0140585;
U.S. Patent Application Publication No. 2014/0151453;
U.S. Patent Application Publication No. 2014/0152882;
U.S. Patent Application Publication No. 2014/0158770;
U.S. Patent Application Publication No. 2014/0159869;
U.S. Patent Application Publication No. 2014/0166755;
U.S. Patent Application Publication No. 2014/0166759;
U.S. Patent Application Publication No. 2014/0168787;
U.S. Patent Application Publication No. 2014/0175165;
U.S. Patent Application Publication No. 2014/0175172;
U.S. Patent Application Publication No. 2014/0191644;
U.S. Patent Application Publication No. 2014/0191913;
U.S. Patent Application Publication No. 2014/0197238;
U.S. Patent Application Publication No. 2014/0197239;
U.S. Patent Application Publication No. 2014/0197304;
U.S. Patent Application Publication No. 2014/0214631;
U.S. Patent Application Publication No. 2014/0217166;
U.S. Patent Application Publication No. 2014/0217180;
U.S. Patent Application Publication No. 2014/0231500;
U.S. Patent Application Publication No. 2014/0232930;
U.S. Patent Application Publication No. 2014/0247315;
U.S. Patent Application Publication No. 2014/0263493;
U.S. Patent Application Publication No. 2014/0263645;
U.S. Patent Application Publication No. 2014/0267609;
U.S. Patent Application Publication No. 2014/0270196;
U.S. Patent Application Publication No. 2014/0270229;
U.S. Patent Application Publication No. 2014/0278387;
U.S. Patent Application Publication No. 2014/0278391;
U.S. Patent Application Publication No. 2014/0282210;
U.S. Patent Application Publication No. 2014/0284384;
U.S. Patent Application Publication No. 2014/0288933;
U.S. Patent Application Publication No. 2014/0297058;
U.S. Patent Application Publication No. 2014/0299665;
U.S. Patent Application Publication No. 2014/0312121;
U.S. Patent Application Publication No. 2014/0319220;
U.S. Patent Application Publication No. 2014/0319221;
U.S. Patent Application Publication No. 2014/0326787;
U.S. Patent Application Publication No. 2014/0332590;
U.S. Patent Application Publication No. 2014/0344943;
U.S. Patent Application Publication No. 2014/0346233;
U.S. Patent Application Publication No. 2014/0351317;
U.S. Patent Application Publication No. 2014/0353373;
U.S. Patent Application Publication No. 2014/0361073;
U.S. Patent Application Publication No. 2014/0361082;
U.S. Patent Application Publication No. 2014/0362184;
U.S. Patent Application Publication No. 2014/0363015;
U.S. Patent Application Publication No. 2014/0369511;
U.S. Patent Application Publication No. 2014/0374483;
U.S. Patent Application Publication No. 2014/0374485;
U.S. Patent Application Publication No. 2015/0001301;
U.S. Patent Application Publication No. 2015/0001304;
U.S. Patent Application Publication No. 2015/0003673;
U.S. Patent Application Publication No. 2015/0009338;
U.S. Patent Application Publication No. 2015/0009610;
U.S. Patent Application Publication No. 2015/0014416;
U.S. Patent Application Publication No. 2015/0021397;
U.S. Patent Application Publication No. 2015/0028102;
U.S. Patent Application Publication No. 2015/0028103;
U.S. Patent Application Publication No. 2015/0028104;
U.S. Patent Application Publication No. 2015/0029002;
U.S. Patent Application Publication No. 2015/0032709;
U.S. Patent Application Publication No. 2015/0039309;
U.S. Patent Application Publication No. 2015/0039878;
U.S. Patent Application Publication No. 2015/0040378;
U.S. Patent Application Publication No. 2015/0048168;
U.S. Patent Application Publication No. 2015/0049347;
U.S. Patent Application Publication No. 2015/0051992;
U.S. Patent Application Publication No. 2015/0053766;
U.S. Patent Application Publication No. 2015/0053768;
U.S. Patent Application Publication No. 2015/0053769;
U.S. Patent Application Publication No. 2015/0060544;
U.S. Patent Application Publication No. 2015/0062366;
U.S. Patent Application Publication No. 2015/0063215;

U.S. Patent Application Publication No. 2015/0063676;
U.S. Patent Application Publication No. 2015/0069130;
U.S. Patent Application Publication No. 2015/0071819;
U.S. Patent Application Publication No. 2015/0083800;
U.S. Patent Application Publication No. 2015/0086114;
U.S. Patent Application Publication No. 2015/0088522;
U.S. Patent Application Publication No. 2015/0096872;
U.S. Patent Application Publication No. 2015/0099557;
U.S. Patent Application Publication No. 2015/0100196;
U.S. Patent Application Publication No. 2015/0102109;
U.S. Patent Application Publication No. 2015/0115035;
U.S. Patent Application Publication No. 2015/0127791;
U.S. Patent Application Publication No. 2015/0128116;
U.S. Patent Application Publication No. 2015/0129659;
U.S. Patent Application Publication No. 2015/0133047;
U.S. Patent Application Publication No. 2015/0134470;
U.S. Patent Application Publication No. 2015/0136851;
U.S. Patent Application Publication No. 2015/0136854;
U.S. Patent Application Publication No. 2015/0142492;
U.S. Patent Application Publication No. 2015/0144692;
U.S. Patent Application Publication No. 2015/0144698;
U.S. Patent Application Publication No. 2015/0144701;
U.S. Patent Application Publication No. 2015/0149946;
U.S. Patent Application Publication No. 2015/0161429;
U.S. Patent Application Publication No. 2015/0169925;
U.S. Patent Application Publication No. 2015/0169929;
U.S. Patent Application Publication No. 2015/0178523;
U.S. Patent Application Publication No. 2015/0178534;
U.S. Patent Application Publication No. 2015/0178535;
U.S. Patent Application Publication No. 2015/0178536;
U.S. Patent Application Publication No. 2015/0178537;
U.S. Patent Application Publication No. 2015/0181093;
U.S. Patent Application Publication No. 2015/0181109;
U.S. patent application Ser. No. 13/367,978 for a Laser Scanning Module Employing an Elastomeric U-Hinge Based Laser Scanning Assembly, filed Feb. 7, 2012 (Feng et al.);
U.S. patent application Ser. No. 29/458,405 for an Electronic Device, filed Jun. 19, 2013 (Fitch et al.);
U.S. patent application Ser. No. 29/459,620 for an Electronic Device Enclosure, filed Jul. 2, 2013 (London et al.);
U.S. patent application Ser. No. 29/468,118 for an Electronic Device Case, filed Sep. 26, 2013 (Oberpriller et al.);
U.S. patent application Ser. No. 14/150,393 for Indicia-reader Having Unitary Construction Scanner, filed Jan. 8, 2014 (Colavito et al.);
U.S. patent application Ser. No. 14/200,405 for Indicia Reader for Size-Limited Applications filed Mar. 7, 2014 (Feng et al.);
U.S. patent application Ser. No. 14/231,898 for Hand-Mounted Indicia-Reading Device with Finger Motion Triggering filed Apr. 1, 2014 (Van Horn et al.);
U.S. patent application Ser. No. 29/486,759 for an Imaging Terminal, filed Apr. 2, 2014 (Oberpriller et al.);
U.S. patent application Ser. No. 14/257,364 for Docking System and Method Using Near Field Communication filed Apr. 21, 2014 (Showering);
U.S. patent application Ser. No. 14/264,173 for Autofocus Lens System for Indicia Readers filed Apr. 29, 2014 (Ackley et al.);
U.S. patent application Ser. No. 14/277,337 for MULTIPURPOSE OPTICAL READER, filed May 14, 2014 (Jovanovski et al.);
U.S. patent application Ser. No. 14/283,282 for TERMINAL HAVING ILLUMINATION AND FOCUS CONTROL filed May 21, 2014 (Liu et al.);
U.S. patent application Ser. No. 14/327,827 for a MOBILE-PHONE ADAPTER FOR ELECTRONIC TRANSACTIONS, filed Jul. 10, 2014 (Hejl);
U.S. patent application Ser. No. 14/334,934 for a SYSTEM AND METHOD FOR INDICIA VERIFICATION, filed Jul. 18, 2014 (Hejl);
U.S. patent application Ser. No. 14/339,708 for LASER SCANNING CODE SYMBOL READING SYSTEM, filed Jul. 24, 2014 (Xian et al.);
U.S. patent application Ser. No. 14/340,627 for an AXIALLY REINFORCED FLEXIBLE SCAN ELEMENT, filed Jul. 25, 2014 (Rueblinger et al.);
U.S. patent application Ser. No. 14/446,391 for MULTIFUNCTION POINT OF SALE APPARATUS WITH OPTICAL SIGNATURE CAPTURE filed Jul. 30, 2014 (Good et al.);
U.S. patent application Ser. No. 14/452,697 for INTERACTIVE INDICIA READER, filed Aug. 6, 2014 (Todeschini);
U.S. patent application Ser. No. 14/453,019 for DIMENSIONING SYSTEM WITH GUIDED ALIGNMENT, filed Aug. 6, 2014 (Li et al.);
U.S. patent application Ser. No. 14/462,801 for MOBILE COMPUTING DEVICE WITH DATA COGNITION SOFTWARE, filed on Aug. 19, 2014 (Todeschini et al.);
U.S. patent application Ser. No. 14/483,056 for VARIABLE DEPTH OF FIELD BARCODE SCANNER filed Sep. 10, 2014 (McCloskey et al.);
U.S. patent application Ser. No. 14/513,808 for IDENTIFYING INVENTORY ITEMS IN A STORAGE FACILITY filed Oct. 14, 2014 (Singel et al.);
U.S. patent application Ser. No. 14/519,195 for HAND-HELD DIMENSIONING SYSTEM WITH FEEDBACK filed Oct. 21, 2014 (Laffargue et al.);
U.S. patent application Ser. No. 14/519,179 for DIMENSIONING SYSTEM WITH MULTIPATH INTERFERENCE MITIGATION filed Oct. 21, 2014 (Thuries et al.);
U.S. patent application Ser. No. 14/519,211 for SYSTEM AND METHOD FOR DIMENSIONING filed Oct. 21, 2014 (Ackley et al.);
U.S. patent application Ser. No. 14/519,233 for HAND-HELD DIMENSIONER WITH DATA-QUALITY INDICATION filed Oct. 21, 2014 (Laffargue et al.);
U.S. patent application Ser. No. 14/519,249 for HAND-HELD DIMENSIONING SYSTEM WITH MEASUREMENT-CONFORMANCE FEEDBACK filed Oct. 21, 2014 (Ackley et al.);
U.S. patent application Ser. No. 14/527,191 for METHOD AND SYSTEM FOR RECOGNIZING SPEECH USING WILDCARDS IN AN EXPECTED RESPONSE filed Oct. 29, 2014 (Braho et al.);
U.S. patent application Ser. No. 14/529,563 for ADAPTABLE INTERFACE FOR A MOBILE COMPUTING DEVICE filed Oct. 31, 2014 (Schoon et al.);
U.S. patent application Ser. No. 14/529,857 for BARCODE READER WITH SECURITY FEATURES filed Oct. 31, 2014 (Todeschini et al.);
U.S. patent application Ser. No. 14/398,542 for PORTABLE ELECTRONIC DEVICES HAVING A SEPARATE LOCATION TRIGGER UNIT FOR USE IN CONTROLLING AN APPLICATION UNIT filed Nov. 3, 2014 (Bian et al.);
U.S. patent application Ser. No. 14/531,154 for DIRECTING AN INSPECTOR THROUGH AN INSPECTION filed Nov. 3, 2014 (Miller et al.);

U.S. patent application Ser. No. 14/533,319 for BARCODE SCANNING SYSTEM USING WEARABLE DEVICE WITH EMBEDDED CAMERA filed Nov. 5, 2014 (Todeschini);

U.S. patent application Ser. No. 14/535,764 for CONCATENATED EXPECTED RESPONSES FOR SPEECH RECOGNITION filed Nov. 7, 2014 (Braho et al.);

U.S. patent application Ser. No. 14/568,305 for AUTOCONTRAST VIEWFINDER FOR AN INDICIA READER filed Dec. 12, 2014 (Todeschini);

U.S. patent application Ser. No. 14/573,022 for DYNAMIC DIAGNOSTIC INDICATOR GENERATION filed Dec. 17, 2014 (Goldsmith);

U.S. patent application Ser. No. 14/578,627 for SAFETY SYSTEM AND METHOD filed Dec. 22, 2014 (Ackley et al.);

U.S. patent application Ser. No. 14/580,262 for MEDIA GATE FOR THERMAL TRANSFER PRINTERS filed Dec. 23, 2014 (Bowles);

U.S. patent application Ser. No. 14/590,024 for SHELVING AND PACKAGE LOCATING SYSTEMS FOR DELIVERY VEHICLES filed Jan. 6, 2015 (Payne);

U.S. patent application Ser. No. 14/596,757 for SYSTEM AND METHOD FOR DETECTING BARCODE PRINTING ERRORS filed Jan. 14, 2015 (Ackley);

U.S. patent application Ser. No. 14/416,147 for OPTICAL READING APPARATUS HAVING VARIABLE SETTINGS filed Jan. 21, 2015 (Chen et al.);

U.S. patent application Ser. No. 14/614,706 for DEVICE FOR SUPPORTING AN ELECTRONIC TOOL ON A USER'S HAND filed Feb. 5, 2015 (Oberpriller et al.);

U.S. patent application Ser. No. 14/614,796 for CARGO APPORTIONMENT TECHNIQUES filed Feb. 5, 2015 (Morton et al.);

U.S. patent application Ser. No. 29/516,892 for TABLE COMPUTER filed Feb. 6, 2015 (Bidwell et al.);

U.S. patent application Ser. No. 14/619,093 for METHODS FOR TRAINING A SPEECH RECOGNITION SYSTEM filed Feb. 11, 2015 (Pecorari);

U.S. patent application Ser. No. 14/628,708 for DEVICE, SYSTEM, AND METHOD FOR DETERMINING THE STATUS OF CHECKOUT LANES filed Feb. 23, 2015 (Todeschini);

U.S. patent application Ser. No. 14/630,841 for TERMINAL INCLUDING IMAGING ASSEMBLY filed Feb. 25, 2015 (Gomez et al.);

U.S. patent application Ser. No. 14/635,346 for SYSTEM AND METHOD FOR RELIABLE STORE-AND-FORWARD DATA HANDLING BY ENCODED INFORMATION READING TERMINALS filed Mar. 2, 2015 (Sevier);

U.S. patent application Ser. No. 29/519,017 for SCANNER filed Mar. 2, 2015 (Zhou et al.);

U.S. patent application Ser. No. 14/405,278 for DESIGN PATTERN FOR SECURE STORE filed Mar. 9, 2015 (Zhu et al.);

U.S. patent application Ser. No. 14/660,970 for DECODABLE INDICIA READING TERMINAL WITH COMBINED ILLUMINATION filed Mar. 18, 2015 (Kearney et al.);

U.S. patent application Ser. No. 14/661,013 for REPROGRAMMING SYSTEM AND METHOD FOR DEVICES INCLUDING PROGRAMMING SYMBOL filed Mar. 18, 2015 (Soule et al.);

U.S. patent application Ser. No. 14/662,922 for MULTIFUNCTION POINT OF SALE SYSTEM filed Mar. 19, 2015 (Van Horn et al.);

U.S. patent application Ser. No. 14/663,638 for VEHICLE MOUNT COMPUTER WITH CONFIGURABLE IGNITION SWITCH BEHAVIOR filed Mar. 20, 2015 (Davis et al.);

U.S. patent application Ser. No. 14/664,063 for METHOD AND APPLICATION FOR SCANNING A BARCODE WITH A SMART DEVICE WHILE CONTINUOUSLY RUNNING AND DISPLAYING AN APPLICATION ON THE SMART DEVICE DISPLAY filed Mar. 20, 2015 (Todeschini);

U.S. patent application Ser. No. 14/669,280 for TRANSFORMING COMPONENTS OF A WEB PAGE TO VOICE PROMPTS filed Mar. 26, 2015 (Funyak et al.);

U.S. patent application Ser. No. 14/674,329 for AIMER FOR BARCODE SCANNING filed Mar. 31, 2015 (Bidwell);

U.S. patent application Ser. No. 14/676,109 for INDICIA READER filed Apr. 1, 2015 (Huck);

U.S. patent application Ser. No. 14/676,327 for DEVICE MANAGEMENT PROXY FOR SECURE DEVICES filed Apr. 1, 2015 (Yeakley et al.);

U.S. patent application Ser. No. 14/676,898 for NAVIGATION SYSTEM CONFIGURED TO INTEGRATE MOTION SENSING DEVICE INPUTS filed Apr. 2, 2015 (Showering);

U.S. patent application Ser. No. 14/679,275 for DIMENSIONING SYSTEM CALIBRATION SYSTEMS AND METHODS filed Apr. 6, 2015 (Laffargue et al.);

U.S. patent application Ser. No. 29/523,098 for HANDLE FOR A TABLET COMPUTER filed Apr. 7, 2015 (Bidwell et al.);

U.S. patent application Ser. No. 14/682,615 for SYSTEM AND METHOD FOR POWER MANAGEMENT OF MOBILE DEVICES filed Apr. 9, 2015 (Murawski et al.);

U.S. patent application Ser. No. 14/686,822 for MULTIPLE PLATFORM SUPPORT SYSTEM AND METHOD filed Apr. 15, 2015 (Qu et al.);

U.S. patent application Ser. No. 14/687,289 for SYSTEM FOR COMMUNICATION VIA A PERIPHERAL HUB filed Apr. 15, 2015 (Kohtz et al.);

U.S. patent application Ser. No. 29/524,186 for SCANNER filed Apr. 17, 2015 (Zhou et al.);

U.S. patent application Ser. No. 14/695,364 for MEDICATION MANAGEMENT SYSTEM filed Apr. 24, 2015 (Sewell et al.);

U.S. patent application Ser. No. 14/695,923 for SECURE UNATTENDED NETWORK AUTHENTICATION filed Apr. 24, 2015 (Kubler et al.);

U.S. patent application Ser. No. 29/525,068 for TABLET COMPUTER WITH REMOVABLE SCANNING DEVICE filed Apr. 27, 2015 (Schulte et al.);

U.S. patent application Ser. No. 14/699,436 for SYMBOL READING SYSTEM HAVING PREDICTIVE DIAGNOSTICS filed Apr. 29, 2015 (Nahill et al.);

U.S. patent application Ser. No. 14/702,110 for SYSTEM AND METHOD FOR REGULATING BARCODE DATA INJECTION INTO A RUNNING APPLICATION ON A SMART DEVICE filed May 1, 2015 (Todeschini et al.);

U.S. patent application Ser. No. 14/702,979 for TRACKING BATTERY CONDITIONS filed May 4, 2015 (Young et al.);

U.S. patent application Ser. No. 14/704,050 for INTERMEDIATE LINEAR POSITIONING filed May 5, 2015 (Charpentier et al.);

U.S. patent application Ser. No. 14/705,012 for HANDS-FREE HUMAN MACHINE INTERFACE RESPONSIVE TO A DRIVER OF A VEHICLE filed May 6, 2015 (Fitch et al.);

U.S. patent application Ser. No. 14/705,407 for METHOD AND SYSTEM TO PROTECT SOFTWARE-BASED NETWORK-CONNECTED DEVICES FROM ADVANCED PERSISTENT THREAT filed May 6, 2015 (Hussey et al.);

U.S. patent application Ser. No. 14/707,037 for SYSTEM AND METHOD FOR DISPLAY OF INFORMATION USING A VEHICLE-MOUNT COMPUTER filed May 8, 2015 (Chamberlin);

U.S. patent application Ser. No. 14/707,123 for APPLICATION INDEPENDENT DEX/UCS INTERFACE filed May 8, 2015 (Pape);

U.S. patent application Ser. No. 14/707,492 for METHOD AND APPARATUS FOR READING OPTICAL INDICIA USING A PLURALITY OF DATA SOURCES filed May 8, 2015 (Smith et al.);

U.S. patent application Ser. No. 14/710,666 for PRE-PAID USAGE SYSTEM FOR ENCODED INFORMATION READING TERMINALS filed May 13, 2015 (Smith);

U.S. patent application Ser. No. 29/526,918 for CHARGING BASE filed May 14, 2015 (Fitch et al.);

U.S. patent application Ser. No. 14/715,672 for AUGMENTED REALITY ENABLED HAZARD DISPLAY filed May 19, 2015 (Venkatesha et al.);

U.S. patent application Ser. No. 14/715,916 for EVALUATING IMAGE VALUES filed May 19, 2015 (Ackley);

U.S. patent application Ser. No. 14/722,608 for INTERACTIVE USER INTERFACE FOR CAPTURING A DOCUMENT IN AN IMAGE SIGNAL filed May 27, 2015 (Showering et al.);

U.S. patent application Ser. No. 29/528,165 for IN-COUNTER BARCODE SCANNER filed May 27, 2015 (Oberpriller et al.);

U.S. patent application Ser. No. 14/724,134 for ELECTRONIC DEVICE WITH WIRELESS PATH SELECTION CAPABILITY filed May 28, 2015 (Wang et al.);

U.S. patent application Ser. No. 14/724,849 for METHOD OF PROGRAMMING THE DEFAULT CABLE INTERFACE SOFTWARE IN AN INDICIA READING DEVICE filed May 29, 2015 (Barten);

U.S. patent application Ser. No. 14/724,908 for IMAGING APPARATUS HAVING IMAGING ASSEMBLY filed May 29, 2015 (Barber et al.);

U.S. patent application Ser. No. 14/725,352 for APPARATUS AND METHODS FOR MONITORING ONE OR MORE PORTABLE DATA TERMINALS (Caballero et al.);

U.S. patent application Ser. No. 29/528,590 for ELECTRONIC DEVICE filed May 29, 2015 (Fitch et al.);

U.S. patent application Ser. No. 29/528,890 for MOBILE COMPUTER HOUSING filed Jun. 2, 2015 (Fitch et al.);

U.S. patent application Ser. No. 14/728,397 for DEVICE MANAGEMENT USING VIRTUAL INTERFACES CROSS-REFERENCE TO RELATED APPLICATIONS filed Jun. 2, 2015 (Caballero);

U.S. patent application Ser. No. 14/732,870 for DATA COLLECTION MODULE AND SYSTEM filed Jun. 8, 2015 (Powilleit);

U.S. patent application Ser. No. 29/529,441 for INDICIA READING DEVICE filed Jun. 8, 2015 (Zhou et al.);

U.S. patent application Ser. No. 14/735,717 for INDICIA-READING SYSTEMS HAVING AN INTERFACE WITH A USER'S NERVOUS SYSTEM filed Jun. 10, 2015 (Todeschini);

U.S. patent application Ser. No. 14/738,038 for METHOD OF AND SYSTEM FOR DETECTING OBJECT WEIGHING INTERFERENCES filed Jun. 12, 2015 (Amundsen et al.);

U.S. patent application Ser. No. 14/740,320 for TACTILE SWITCH FOR A MOBILE ELECTRONIC DEVICE filed Jun. 16, 2015 (Bandringa);

U.S. patent application Ser. No. 14/740,373 for CALIBRATING A VOLUME DIMENSIONER filed Jun. 16, 2015 (Ackley et al.);

U.S. patent application Ser. No. 14/742,818 for INDICIA READING SYSTEM EMPLOYING DIGITAL GAIN CONTROL filed Jun. 18, 2015 (Xian et al.);

U.S. patent application Ser. No. 14/743,257 for WIRELESS MESH POINT PORTABLE DATA TERMINAL filed Jun. 18, 2015 (Wang et al.);

U.S. patent application Ser. No. 29/530,600 for CYCLONE filed Jun. 18, 2015 (Vargo et al);

U.S. patent application Ser. No. 14/744,633 for IMAGING APPARATUS COMPRISING IMAGE SENSOR ARRAY HAVING SHARED GLOBAL SHUTTER CIRCUITRY filed Jun. 19, 2015 (Wang);

U.S. patent application Ser. No. 14/744,836 for CLOUD-BASED SYSTEM FOR READING OF DECODABLE INDICIA filed Jun. 19, 2015 (Todeschini et al.);

U.S. patent application Ser. No. 14/745,006 for SELECTIVE OUTPUT OF DECODED MESSAGE DATA filed Jun. 19, 2015 (Todeschini et al.);

U.S. patent application Ser. No. 14/747,197 for OPTICAL PATTERN PROJECTOR filed Jun. 23, 2015 (Thuries et al.);

U.S. patent application Ser. No. 14/747,490 for DUAL-PROJECTOR THREE-DIMENSIONAL SCANNER filed Jun. 23, 2015 (Jovanovski et al.); and U.S. patent application Ser. No. 14/748,446 for CORDLESS INDICIA READER WITH A MULTIFUNCTION COIL FOR WIRELESS CHARGING AND EAS DEACTIVATION, filed Jun. 24, 2015 (Xie et al.).

While there is shown and described herein certain exemplary embodiments of a monitoring user biometric parameters with nanotechnology in personal locator beacons, it will be manifest to those of ordinary skill in the art that various modifications and rearrangements of the parts may be made without departing from the spirit and scope of the underlying inventive concept and that the same is not limited to the particular forms herein shown and described except insofar as indicated by the scope of the appended claims.

What is claimed is:

1. A personal locator beacon system comprising:
   at least one sensor adapted to detect a biometric parameter of a user; and
   a personal locator beacon communicatively coupled to the at least one sensor and associated with the user, the personal locator beacon configured to receive from the at least one sensor, the biometric parameter, an identifier of the at least one sensor, and at least one of a current geographical location information of the at least one sensor and a third associated time stamp, and a past geographical location information of the at least one sensor and a fourth associated time stamp, second route information for the user, and a second speed of travel for the user, wherein the personal locator beacon comprises:

a first global positioning subsystem adapted to generate current geographical location information of the personal locator beacon and a first timestamp associated with the current geographical location information, wherein the first global positioning subsystem comprises a first static memory configured to store at least one of:

the current geographical location information and the first time stamp associated with the current geographical location information, past geographical location information and a second time stamp associated with the past geographical location information, first route information for the user, and a first speed of travel for the user; and a second global positioning subsystem adapted to generate the current geographical location information of the at least one sensor, wherein the second global positioning subsystem comprises a second static memory to store the at least one of:

the current geographical location information of the at least one sensor and the third time stamp associated with the current geographical location information of the at least one sensor, the past geographical location information of the at least one sensor and the fourth time stamp associated with the past geographical location information of the at least one sensor, the second route information for the user, and the second speed of travel for the user; and wherein the personal locator beacon further comprises a transceiver configured to broadcast, to a communication system associated with a responder, a distress signal comprising the biometric parameter detected by the at least one sensor, the identifier of the at least one sensor and further comprising the current geographical location information and the past geographical location information of the personal locator beacon generated by the first global positioning subsystem, the at least one of the fourth time stamp, the second route information for the user, and the second speed of travel for the user, and at least one of: the first time stamp, the second time stamp, the first route information for the user, and the first speed of travel for the user, wherein the distress signal is broadcasted to determine a geographical location of the user, and facilitate identification of an equipment to aid the user, based on the biometric parameter of the user and the identifier of the at least one sensor.

2. The personal locator beacon system of claim 1, wherein the personal locator beacon further comprises:

a first low energy transceiver;

a first low energy antenna, wherein the first low energy transceiver is communicatively coupled to the first low energy antenna; and a first microprocessor communicatively coupled to the first low energy transceiver, and wherein the at least one sensor comprises:

a second low energy antenna;

a second low energy transceiver;

a second microprocessor communicatively coupled to the second low energy transceiver;

and wherein the first low energy transceiver, the first low energy antenna, the second low energy transceiver, and the second low energy antennae, are low energy Bluetooth components.

3. The personal locator beacon system of claim 2, wherein the personal locator beacon is communicatively coupled to the at least one sensor through the first low energy transceiver and antenna and the second low energy transceiver and antenna.

4. The personal locator beacon system of claim 1, wherein the at least one sensor comprises: a bioimpedance sensor configured to measure one or more of a user heart rate, respiration level, or hydration level.

5. The personal locator beacon system of claim 1, wherein the at least one sensor comprises an optical heart rate sensor.

6. The personal locator beacon system of claim 1, wherein the at least one sensor comprises a galvanic skin response sensor configured to monitor user sweat levels.

7. The personal locator beacon system of claim 1, wherein the at least one sensor comprises an accelerometer configured to count user steps or record changes in movement.

8. The personal locator beacon system of claim 1, wherein the at least one sensor comprises a gyroscope configured to measure orientation of the user.

9. The personal locator beacon system of claim 1, wherein the at least one sensor comprises a thermometer configured to monitor user body temperature.

10. The personal locator beacon system of claim 1, wherein the at least one sensor comprises a radiation sensor configured to measure user radiation exposure.

11. The personal locator beacon system of claim 10, wherein the radiation sensor measures user radiation exposure to ultra-violet, high-energy beta, gamma, x-ray frequencies, or any combinations thereof.

12. The personal locator beacon system of claim 2, wherein each of the first and second global positioning subsystems comprises:

a GPS receiver, a GPS antenna, and the first static memory and the second static memory communicatively coupled to the first GPS receiver and the second GPS receiver.

13. The personal locator beacon system of claim 12, the personal locator beacon comprising a beacon static memory communicatively coupled to the first microprocessor, being configured to receive and store data from the at least one sensor for a period of configurable days.

14. The personal locator beacon system of claim 1, wherein the at least one sensor is located on a wearable device comprising a glove, a wristband, a necklace, a headband, a hat, smartphone, smartwatch or a chest strap.

15. The personal locator beacon system of claim 1, wherein the at least one sensor is located on a portable device carriable in a beltpack, backpack, or other external container.

16. A method of monitoring user biometric parameters in a personal locator beacon system, the method comprising:

associating a personal locator beacon with a user;

coupling the personal locator beacon to a sensor that detects a biometric parameter of the user;

determining a first geographical information by a first global positioning subsystem, wherein the first geographical information comprises current geographical location information and past geographical location information of the personal locator beacon;

determining a second geographical information by a second global positioning subsystem, wherein the second geographical information comprises current geographical location information and past geographical location information of the sensor;

storing at least one of:

the first geographical information,
the second geographical information,
a first time stamp and a second time stamp associated with the current geographical location information and the past geographical location information of the personal locator beacon, respectively,
a third time stamp and a fourth time stamp associated with the current geographical location information and the past geographical location information of the sensor, respectively,
a route information for the user, and
a speed of travel for the user;
communicating to the personal locator beacon from the sensor the biometric parameter of the user, an identifier of the sensor, and at least one of: the current geographical location information of the sensor and the third time stamp, and the past geographical location information of the sensor and the fourth time stamp; and
broadcasting, to a communication system associated with a responder, from the personal locator beacon, a distress signal comprising the biometric parameter of the user and the identifier of the sensor and further comprising the first geographical information, the at least one of the current geographical location information of the sensor and the third time stamp, and the past geographical location information of the sensor and the fourth time stamp, and least one of: the first time stamp, the second time stamp the route information for the user, and the speed of travel for the user, wherein the distress signal is broadcasted to determine a geographical location of the user, and facilitate identification of an equipment to aid the user, based on the biometric parameter of the user and the identifier of the sensor.

17. The method of claim 16, wherein each of the personal locator beacon and the sensor comprises the first global positioning system and the second global positioning subsystem respectively, having:
   a GPS receiver,
   a GPS antenna, and
   a static memory coupled to the GPS receiver.

18. The method of claim 16, wherein the sensor includes at least one of:
   a bioimpedance sensor configured to measure one or more biometric parameters of the user including, user heart rate, respiration level, or hydration level;
   an optical heart rate sensor configured to measure a biometric parameter of a user heart rate;
   a galvanic skin response sensor configured to monitor a biometric parameter of user sweat level;
   an accelerometer configured to measure a biometric parameter of user steps or changes in user movement;
   a gyroscope configured to measure a biometric parameter of a user orientation;
   a thermometer configured to monitor a biometric parameter of user body temperature;
   a radiation sensor configured to monitor user radiation exposure levels; or any combination thereof.

19. The method of claim 16, wherein the sensor is located on a wearable device comprising a glove, a wristband, a necklace, a headband, a hat, smartphone, smartwatch, or a chest strap.

20. The method of claim 16, wherein the personal locator beacon is wirelessly coupled to the sensor using Bluetooth low energy.

21. The method of claim 16, wherein the biometric parameter of the user, the identifier of the sensor and the at least one of the current geographical location information of the sensor and the third time stamp, and the past geographical location information of the sensor and the fourth time stamp, are communicated from the sensor to the personal locator beacon at configured intervals and wherein the configured intervals are event triggered intervals, predetermined fixed intervals: profile based intervals, or any combination thereof.

22. The method of claim 16, wherein the personal locator beacon is a Cospas-Sarsat distress beacon or a vehicle-mounted satellite-based communication relay.

23. The method of claim 16, wherein the distress signal comprises geographical location of the sensor, geographical information of the personal locator beacon, and the biometric parameter of the user.

24. The personal locator beacon system of claim 1, wherein the biometric parameter of the at least one sensor, the identifier of the at least one sensor, and the at least one of the current geographical location information information of the at least one sensor and the fourth time slam the second route information for the user, and the second speed of travel for the user, are communicated to the personal locator beacon at configured intervals and wherein the configured intervals are event triggered intervals, predetermined fixed intervals, profile based intervals, or any combination thereof.

* * * * *